US011155786B2

(12) United States Patent
Wälchli et al.

(10) Patent No.: US 11,155,786 B2
(45) Date of Patent: Oct. 26, 2021

(54) UNIVERSAL KILLER T-CELL

(71) Applicant: Oslo Universitetssykehus HF, Oslo (NO)

(72) Inventors: Sébastien Wälchli, Oslo (NO); Else Marit Inderberg Suso, Oslo (NO); Gustav Gaudernack, Sandvika (NO); Gunnar Kvalheim, Oslo (NO)

(73) Assignee: Oslo Universitetssykehus HF, Oslo (NO)

( * ) Notice: Subject to any disclaimer, the term of this patent is extended or adjusted under 35 U.S.C. 154(b) by 21 days.

(21) Appl. No.: 15/545,021

(22) PCT Filed: Jan. 22, 2016

(86) PCT No.: PCT/EP2016/051344
§ 371 (c)(1),
(2) Date: Jul. 20, 2017

(87) PCT Pub. No.: WO2016/116601
PCT Pub. Date: Jul. 28, 2016

(65) Prior Publication Data
US 2018/0010097 A1    Jan. 11, 2018

(30) Foreign Application Priority Data

Jan. 23, 2015  (GB) ..................................... 1501175

(51) Int. Cl.
| | |
|---|---|
| *A61K 35/17* | (2015.01) |
| *C12N 5/0783* | (2010.01) |
| *C12N 5/10* | (2006.01) |
| *C12N 15/12* | (2006.01) |
| *C07K 14/725* | (2006.01) |

(52) U.S. Cl.
CPC ............ *C12N 5/0646* (2013.01); *A61K 35/17* (2013.01); *C07K 14/7051* (2013.01); *C12N 2501/515* (2013.01); *C12N 2502/99* (2013.01)

(58) Field of Classification Search
None
See application file for complete search history.

(56) References Cited

U.S. PATENT DOCUMENTS

| | | | |
|---|---|---|---|
| 5,124,251 A | 6/1992 | Lanier et al. | |
| 7,618,817 B2 | 11/2009 | Campbell | |
| 2006/0292156 A1* | 12/2006 | Campbell | A61K 49/00 424/155.1 |
| 2009/0104170 A1* | 4/2009 | Childs | C12N 5/0646 424/93.71 |
| 2010/0159594 A1 | 6/2010 | Hansen et al. | |
| 2012/0015888 A1* | 1/2012 | Rosenberg | C07K 14/705 514/19.3 |
| 2013/0273083 A1* | 10/2013 | Parenteau | C07K 14/70503 424/184.1 |
| 2017/0274014 A1* | 9/2017 | Brogdon | A61K 39/39558 |

FOREIGN PATENT DOCUMENTS

| | | |
|---|---|---|
| JP | 2015-223143 A | 12/2015 |
| WO | 98/49268 A1 | 11/1998 |
| WO | 00/31239 A1 | 6/2000 |
| WO | 03/048337 A2 | 6/2003 |
| WO | 2006/023148 | 3/2006 |
| WO | 2014/037422 A1 | 3/2014 |
| WO | 2014/117121 A1 | 7/2014 |
| WO | 2014/121264 A1 | 8/2014 |
| WO | 2015/193411 A1 | 12/2015 |

OTHER PUBLICATIONS

Hall et al. Requirements for Cell Surface Expression of the Human TCR/CD3 Complex in Non-T-Cells. International Immunology, 1991. 3(4):359-368.*
Anzar et al, Intratumoral Delivery of Immunotherapy—Act Locally, Think Globally, J Immunol 2017; 198:31-39.*
Patterson et al, Human Invariant NKT Cells Display Alloreactivity Instructed by Invariant TCR-CD1d Interaction and Killer Ig Receptors, The Journal of Immunology, 2008, 181: 3268-3276.*
Weidanz et al, TCR-Like Biomolecules Target Peptide/MHC Class I Complexes on the Surface of Infected and Cancerous Cells, Int Rev Immunol. 2011 ; 30(5-6): 328-340.*
Zhang, G, Retargeting NK-92 for anti-melanoma activity by a TCR-like single-domain antibody, Immunology and Cell Biology (2013) 91,615-624.*
Lanier, L.L. European J of Immunology,Commentary: Back to the future—defining NK cells and T cells 2007, pp. 1424-1426.*
Pievani et al, Dual-functional capability of CD3+CD56+ CIK cells, a T-cell subset that acquires NK function and retains TCR-mediated specific cytotoxicity, Blood, 2011, pp. 3301-3310.*
Phillips, J.H., et al., "Ontogeny of Human Natural Killer (NK) Cells: Fetal NK Cells Mediate Cytolytic Function and Express Cytoplasmic CD3ε,δ Proteins", J. Exp. Med., Apr. 1992, vol. 175, pp. 1055-1066.

(Continued)

*Primary Examiner* — Maria Marvich
(74) *Attorney, Agent, or Firm* — McDonnell Boehnen Hulbert & Berghoff LLP

(57) ABSTRACT

The present invention relates to a modified natural killer (NK) cell and its use in personalised medicine. The modified NK cells of the present invention are non-immunogenic, meaning that they are able to be administered to any recipient subject without being rejected by the host immune system (they are "universal"). In a first embodiment the non-immunogenic NK cells are modified to express CD3 to allow a T-cell Receptor (TcR) to be expressed. In a further embodiment the non-immunogenic NK cells are further modified to express a TcR together with the CD3 co-receptor. Co-expression of CD3 with a specific TcR results in the modified NK cells showing antigen-specific cytotoxicity towards target cells. Universal NK cells can thus be targeted against specific antigens, and may thus be used in personalised medicine, particularly in the field of oncology.

16 Claims, 9 Drawing Sheets
Specification includes a Sequence Listing.

(56) References Cited

OTHER PUBLICATIONS

Rajalingam, Raja, "Overview of the Killer Cell Immunoglobulin-Like Receptor System", Immunogenetics: Methods and Applications in Clinical Practice, Chapter 23; Methods in Molecular Biology, 2012, vol. 882, pp. 391-414.

Lai et al., "Alterations in Expression and Function of Signal-transducing Proteins in Tumor-associated T and Natural Killer Cells in Patients with Ovarian Carcinoma," Clinical Cancer Research, Jan. 1996, pp. 161-173, vol. 2.

Renard et al., "Normal development and function of natural killer cells in CD3 epsilon delta 5/delta 5 mutant mice," Proc. Natl. Acad. Sci. USA, Aug. 1995, pp. 7545-7549, vol. 92, No. 16.

Schirrmann et al., "Human natural killer cell line modified with a chimeric immunoglobulin T-cell receptor gene leads to tumor growth inhibition in vivo," Cancer Gene Therapy, 2002, pp. 390-398, vol. 9, No. 4.

Uherek et al., "Retargeting of natural killer-cell cytolytic activity to ErbB2-expressing cancer cells results in efficient and selective tumor cell destruction," Blood, Aug. 2002, pp. 1265-1273, vol. 100, No. 4.

Ahmadi, M., et al., "CD3 Limits the Efficacy of TCR Gene Therapy In Vivo", Blood, 2011, vol. 118(13), pp. 3528-3537, doi:10.1182/blood-2011-04-346338.

Anderson, P., et al., "CD3-Negative Natural Killer Cells Express ζ TCR as Part of a Novel Molecular Complex", Nature, Sep. 14, 1989, vol. 341, pp. 159-162.

De Smedt, M., et al., "Notch Signaling Induces Cytoplasmic CD3ε Expression in Human Differentiating NK Cells", Blood, Oct. 1, 2007, vol. 110(7), pp. 2696-2704, DOI:10.1182/blood-2007-03-082206.

Gong, J-H., et al., "Characterization of a Human Cell Line (NK-92) with Phenotypical and Functional Characteristics of Activated Natural Killer Cells", Leukemia, Apr. 1994, vol. 8(4), pp. 652-658.

Lanier, L., et al., "Expression of Cytoplasmic CD3 Epsilon Proteins in Activated Human Adult Natural Killer (NK) Cells and CD3 Gamma, Delta, Epsilon Complexes in Fetal NK Cells. Implications for the Relationship of NK and T Lymphocytes.", The Journal of Immunology, Sep. 5, 1992, vol. 149(6), pp. 1876-1880.

Tonn, T., et al., "Treatment of Patients with Advanced Cancer with the Natural Killer Cell Line NK-92", Cytotherapy, 2013, vol. 15(12), pp. 1563-1570.

Vogel, B., et al., "Efficient Generation of Human Natural Killer Cell Lines by Viral Transformation", Leukemia, 2014, vol. 28(1), pp. 192-195, doi:10.1038/leu.2013.188.

Willemsen, R., et al., "Grafting Primary Human T Lymphocytes with Cancer-Specific Chimeric Single Chain and Two Chain TCR", Gene Therapy, 2000, vol. 7, pp. 1369-1377.

U.K. Search Report dated Oct. 13, 2015, received from the U.K. Intellectual Property Patent Office, for European Application No. GB1501175.2, pp. 1-4.

Knorr, D.A., et al., "Pluripotent Stem Cell-Derived Natural Killer Cells for Cancer Therapy", Translational Research, Sep. 2010, vol. 156(3), pp. 147-154.

Walseng, E., et al., "A TCR-Based Chimeric Antigen Receptor", Scientific Reports, Aug. 2017, vol. 7, Article 10713, pp. 1-12, doi:10.1038/s41598-017-11126-y.

EPO Official Action dated Aug. 22, 2019, from the European Patent Office, for European Patent Application 16701339.0, pp. 1-6.

Hall, C., et al., "Requirements for Cell Surface Expression of the Human TCR/CD3 Complex in Non-T Cells", Int. Immunol., Apr. 1991, vol. 3(4), pp. 359-368 (Abstract only).

Tam, Y.K., et al., "Ex Vivo Expansion of the Highly Cytotoxic Human Natural Killer Cell Line NK-92 Under Current Good Manufacturing Practice Conditions for Clinical Adoptive Cellular Immunotherapy", Cytotherapy, 2003, vol. 5(3), pp. 259-272.

Johnson, L.A., et al., "Gene Transfer of Tumor-Reactive TCR Confers Both High Avidity and Tumor Reactivity to Nonreactive Peripheral Blood Mononuclear Cells and Tumor-Infiltrating Lymphocytes", The Journal of Immunology, 2006, vol. 177, pp. 6548-6559.

Yu, Y.Y.L., et al., "Cutting Edge: Single-Chain Trimers of MHC Class I Molecules Form Stable Structures that Potently Stimulate Antigen-Specific T Cells and B Cells", J. Immunol., 2002, vol. 168, pp. 3145-3149.

Abel, A.M., et al., "Natural Killer Cells: Development, Maturation, and Clinical Utilization", Front. Immunol., Aug. 2018, vol. 9, Article 1869, pp. 1-23.

Imai, C., et al., "Genetic Modification of Primary Natural Killer Cells Overcomes inhibitory Signals and Induces Specific Killing of Leukemic Cells", Blood, Jul. 1, 2005, vol. 106(1), pp. 376-383.

Krijgsman, D., et al., "The Role of Natural Killer T-Cells in Cancer—A Phenotypical and Functional Approach", Front. Immunol., Feb. 2018, vol. 9, Article 367, pp. 1-21.

Kruschinski, A., et al., "Engineering Antigen-Specific Primary Human NK Cells Against HER-2 Positive Carcinomas", PNAS, Nov. 11, 2008, vol. 105(45), p. 17481-17486.

Shah, D.K., "T-Cell Development in the Thymus", BiteSized Immunology, British Society for Immunology, 2014, 1 page.

* cited by examiner

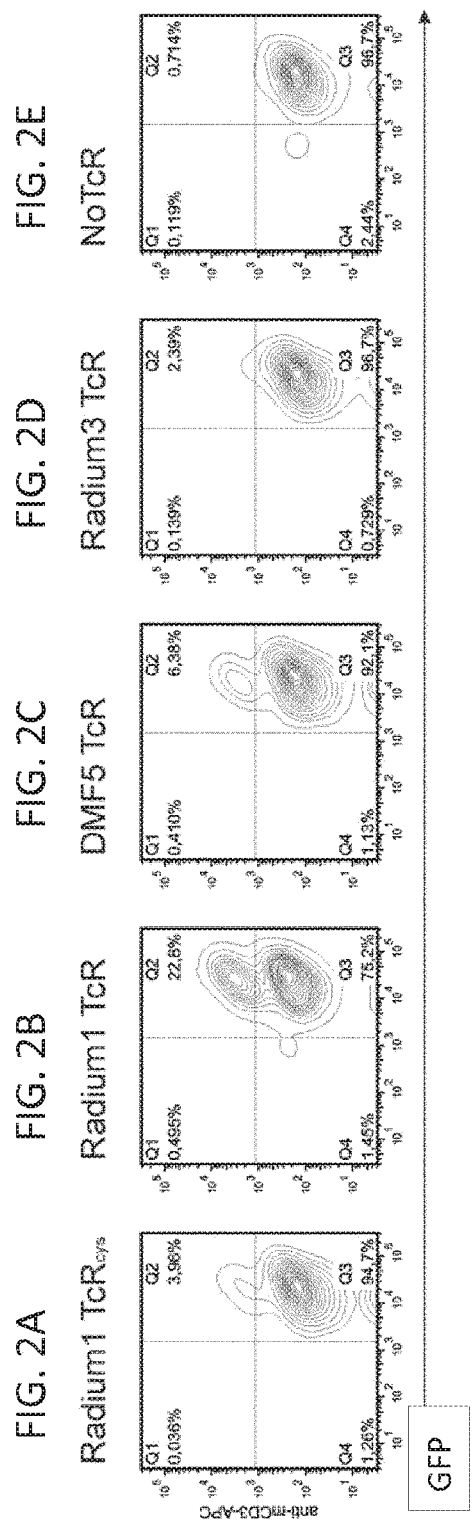

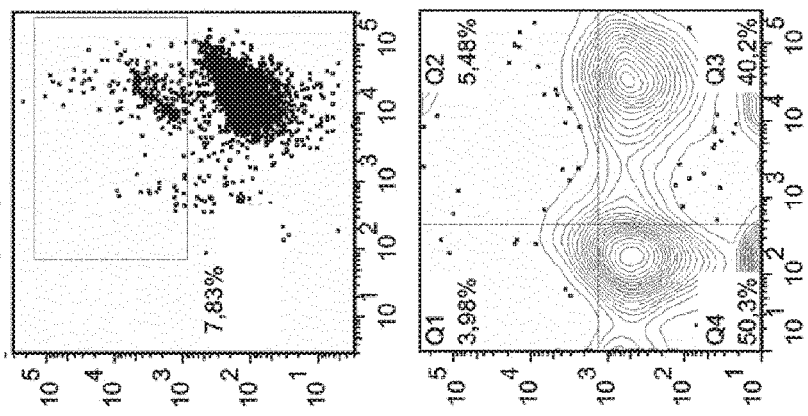
FIG. 3A NoTcR
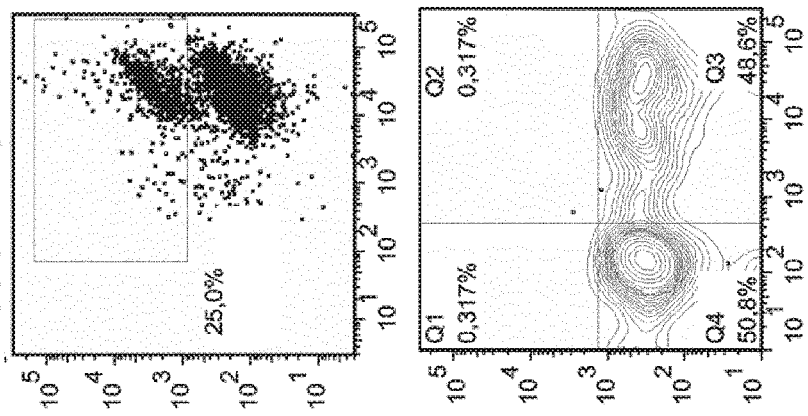
FIG. 3B Radium1 TcR
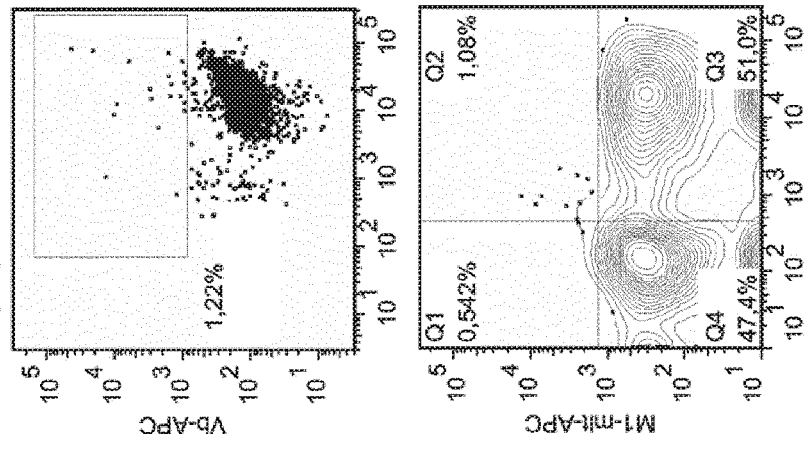
FIG. 3C DMF5 TcR No APC SCT-irr SCT-TgfbRII CD107a Figure 5
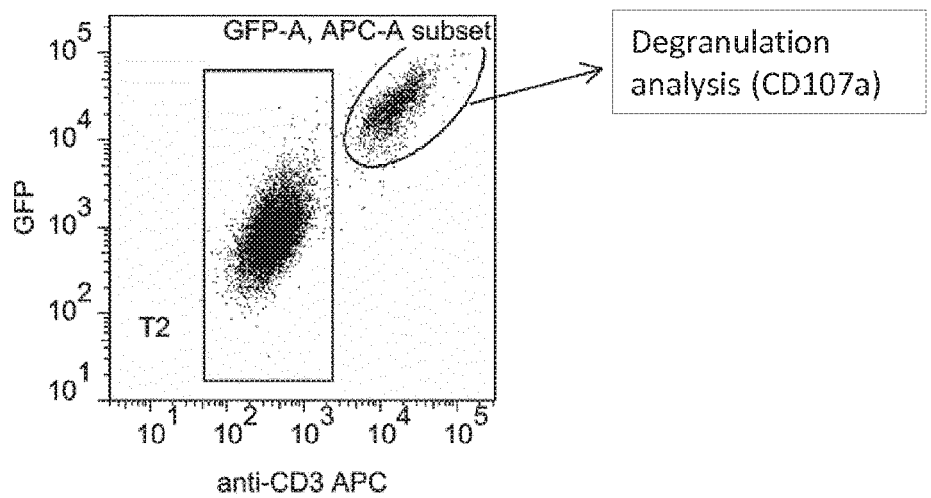
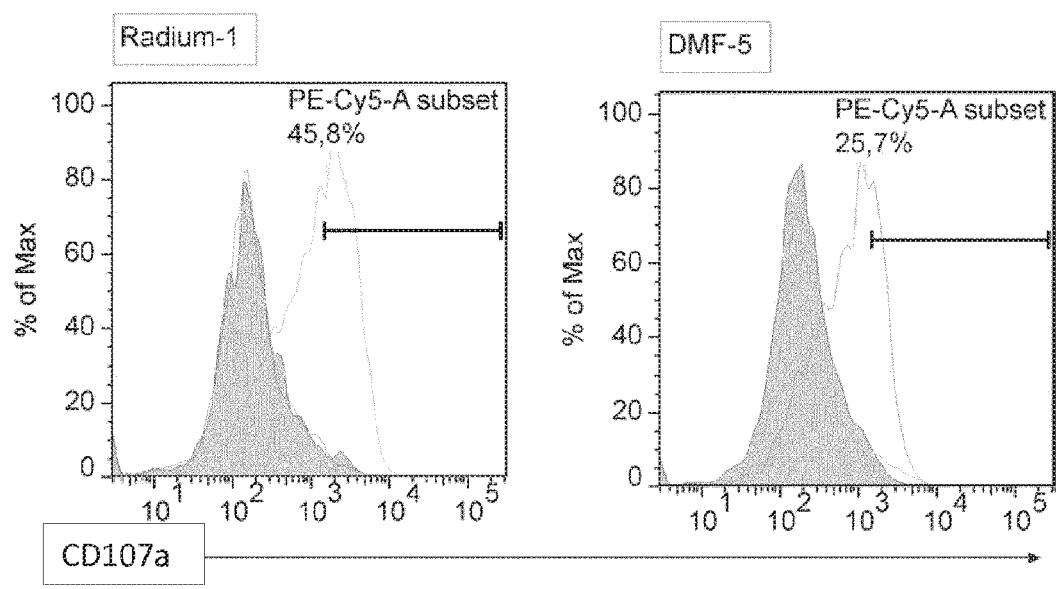

UNIVERSAL KILLER T-CELL

CROSS-REFERENCE

This application is a section 371 of International application no. PCT/EP2016/051344, filed Jan. 22, 2016, which claims priority from GB Patent application no. 1501175.2, filed Jan. 23, 2015, which is incorporated by reference in its entirety.

Sequence Listing Statement

A computer readable form of the Sequence Listing is filed with this application by electronic submission and is incorporated into this application b reference in its entirety. The Sequence Listing is contained in the file created on Jan. 14, 2021, having the file name "17-1026-WO-US Sequence-Listing ST25.txt" and is 558 bytes in size.

FIELD

This invention relates to natural killer cells and their use in therapy, particularly in the treatment of cancer. Specifically a modified natural killer cell has been developed, which has been modified to express CD3 and which may further be modified to co-express an antigen receptor based on a T-cell receptor specific for a cancer antigen, or other target antigen. The modified natural killer cell is non-immunogenic, e.g. expresses low levels of MHC or is MHC-negative, which means that the cells are suitable for universal use, irrespective of the MHC-type of the subject. The invention thus advantageously combines the features of universality and personalisation; the T-cell receptor may be matched to both to the disease condition (e.g. cancer type) and the MHC type of the subject to be treated, allowing the "universal cells" to be used in a treatment which is personalised to the subject to be treated.

BACKGROUND

Certain cells of the immune system demonstrate cytotoxic activity against particular target cells. Cytotoxic T-lymphocytes express T-cell receptors (TcRs) that are capable of specifically recognising antigen-derived peptides bound to MHC class I molecules. By contrast, natural killer (NK) cells are not MHC-restricted and do not require antigen presentation by MHC molecules to exert their killing effect. They are able to recognise stressed cells in the absence of peptide-loaded MHC, and to kill cells lacking MHC. NK cells thus play an important role in innate immunity, as these "non-MHC" cells would otherwise not be detected and destroyed by other immune cells.

Cytotoxic T-cells (also known as cytotoxic T lymphocytes or killer T-cells) are capable of recognising infected or damaged cells in an antigen-specific manner via the TcR by binding to antigens (peptides) presented at the cell surface by MHC class-I molecules. Binding to the peptide-MHC class-I is mediated by the CD8 co-receptor, which enhances the affinity of the binding interaction and increases signal transduction by the TcR. The TcRs of other T-cell types, notably helper T-cells, recognise antigenic peptides presented by MHC-class-II molecules, mediated by the CD4 co-receptor. CD3 is required in T-cells for the localisation of the TcR to the cell surface (Ahmadi et al. 2011. Blood 118, 3528-3537), and is required for activation of a T-cell upon contact with an MHC protein loaded with a suitable antigen peptide. CD3 is a protein complex composed of four distinct chains: a CD3γ chain, a CD3δ chain, two CD3ε chains and the ζ chain, which together with the TcR form the TcR complex.

NK cells (also defined as 'large granular lymphocytes') represent a cell lineage differentiated from the common lymphoid progenitor (which also gives rise to B lymphocytes and T lymphocytes). Unlike T-cells, NK cells do not naturally comprise CD3 at the plasma membrane. Importantly, NK cells do not express a TCR and typically also lack other antigen-specific cell surface receptors (as well as TCRs and CD3, they also do not express immunoglobulin B-cell receptors, and instead typically express CD16 and CD56). Thus NK cells are differentiated by their $CD3^-$, $CD56^+$ phenotype. NK cell cytotoxic activity does not require sensitization but is enhanced by activation with a variety of cytokines including IL-2. NK cells are generally thought to lack appropriate or complete signalling pathways necessary for antigen-receptor-mediated signalling, and thus are not thought to be capable of antigen receptor-dependent signalling, activation and expansion NK cells are cytotoxic, and balance activating and inhibitory receptor signalling to modulate their cytotoxic activity. For instance, NK cells expressing CD16 (the FcγRIII receptor) may bind to the Fc domain of antibodies bound to an infected cell, resulting in NK cell activation. By contrast, activity is reduced against cells expressing high levels of MHC class I proteins. On contact with a target cell NK cells release proteins such as perforin, and enzymes such as proteases (granzymes). Perforin can form pores in the cell membrane of a target cell, inducing apoptosis or cell lysis.

A number of T-cell-based therapies for treating cancer have been developed, and these treatments, known as adoptive cell transfer (ACT) have become increasingly attractive during recent years. Three main ACT strategies have been exploited thus far. The first of these, and the most developed, involves the isolation of patient's own tumour-reactive T-cells from peripheral or tumour sites (known as Tumour Infiltrating Lymphocytes (TILs)). These cells are expanded ex vivo and re-injected into a patient. However, this method can involve delays of several weeks whilst the cells are expanded, and requires specialist cell production facilities.

Two alternative therapies are available, which involve modification of a patient's own T-cells with receptors capable of recognising a tumour. In one option, TcRs having activity towards a cancer antigen can be isolated and characterised, and a gene encoding the TcR can be inserted into T-cells and re-injected into a patient. This therapy has been shown to shrink solid tumours in some patients, but is associated with a significant drawback: the TcRs used must be matched to a patient's immune type. Accordingly, as an alternative to the use of TcRs, therapies involving the expression of Chimeric Antigen Receptors (CARs) in T-cells have also been suggested. CARs are fusion proteins comprising an antibody linked to the signalling domain of the TcR complex, and can be used to direct T cells against a tumour if a suitable antibody is selected. Unlike a TCR, a CAR does not need to MHC-matched to the recipient. However, very few cancer-specific surface antigens have thus far been identified which can be used as suitable targets for CARs, and thus the use of CARs in cancer therapies is limited at present.

All ACT approaches involving the modification of a T-cell with a TcR or a CAR require the isolation and modification of T-cells from a patient, or from a tissue-type matched donor. The use of autologous T-cells is necessary in order to avoid the risk of rejection if non-autologous cells are used.

This increases the costs associated with ACT, and can also increase the time scale required in order to prepare T-cells for use in ACT.

Alternative methods seeking to overcome the above limitations of ACT utilise cytotoxic NK cells, as described for example in WO 98/49268. NK cells are potent killing cells and are highly cytotoxic against a number of different malignant cells. Since NK cells will recognise target cells which express non-self HLA molecules, but not self HLA antigens, autologous NK cells are not generally effective and allogeneic NK cells (which necessitates the careful removal of T-cells to avoid GvHD) or cell lines need to be used. Therapies based upon irradiated cells of the NK cell line NK-92 have progressed to clinical trials in the treatment of leukaemias and other haematological malignancies. Irradiation means that the cells are unable to proliferate and hence the killing effect is of limited and defined duration. The NK cells also do not attack healthy tissues. However, the natural "range" of NK cells is limited and although NK-92 cells have a broader range than primary NK cells, as NK cells do not naturally comprise receptors suitable for specifically targeting an antigen on a target cell, further modification of these cells is required in order to extend the range of cancers that may be treated and to target, or re-direct the cells against, a particular or selected cancer. Such re-direction means of course that the requirement for allogeneic NK cells is removed, but NK-cell lines may still nonetheless have advantages, e.g. improved cytotoxicity, as compared to primary or autologous NK cells.

To this end NK cells expressing CARs have been developed for use in the treatment of cancer. CARs which recognise antigens on the surface of cancer cells have been introduced into the continuously growing NK-92 cell line, and NK-92 cells comprising these CARs have been shown to have enhanced cytotoxicity for tumour cells relative to parental NK-92 cells (Uherek et al. 2002. Blood 200, 1265-1273). Early clinical trials are ongoing. However, as noted above, the lack of available antigens as targets for CARs presently limits the use the CAR- based therapies.

SUMMARY

The present invention is based on an alternative approach to provide cancer-specific killing cells. More particularly, the present invention aims to provide cancer-specific killer cells, based on NK cells, for universal use, meaning that the cells do not have to be matched to the immune type of the subject to be treated, as is presently required for T-cell-based therapies, but they may nonetheless be tailored to the specific immune- and cancer-type of the subject, according to need. Thus, the universal killer cells may be used for personalised medicine.

The present invention thus proposes to change a NK cell to a T-cell, and therefore to render it able to express a TcR and kill cells in a specific and directed way, like a T-cell. The present invention combines the potency and inherent natural killing ability of NK cells with the specific targeting and cell activation afforded by the TcR. Although CARs have previously been expressed in NK cells, it has not heretofore been thought possible that an NK cell would possess all the necessary signalling pathways and machinery to allow a TcR to be successfully expressed in a manner which results in successful activation and targeted killing by the NK cell. Universality is provided by using an NK cell which is non-immunogenic, e.g. which naturally expresses low levels of MHC, or which has reduced proliferative capacity, or by rendering the NK cell MHC- (e.g. HLA-) negative, such that the cell is not recognised as foreign by the immune system of the recipient. Thus the NK cell does not need to be matched to the immune- (e.g. HLA-) type of the subject being treated and may be administered universally, regardless of the immune type of the subject (i.e. to a subject having any immune type, e.g. any HLA profile/type).

The present invention thus provides means which allow a functional, active TcR to be expressed in a non-immunogenic NK cell. In this way a universal killer T-cell may be provided which does not depend on MHC-matching of the cell, but which has controlled specificity dictated by the specificity of the TcR which is introduced into the cell. Co-expression of CD3 and a TcR in NK cells was found to be sufficient for the TcR to localise to the surface of NK cells, and surprisingly the NK cell expressing the TcR demonstrated antigen-specific cytotoxicity towards target cells. Viewed another way, the present invention provides means to convert an NK cell into a cytotoxic T-cell with the added benefits of universality, simply through the co-expression of CD3 and a TcR in a non-immunogenic NK cell. The present invention thus provides a 'universal' killer T-cell, which can be used in personalised medicine.

DESCRIPTION OF THE DRAWINGS

The present invention may be more fully understood from the Examples below and in reference to the drawings, in which:

FIGS. 2A-2E show that CD3 can be detected at the surface of NK-92 cells expressing CD3-IRES-GFP, in the presence of a TcR. GFP$^+$ sorted NK-92 (NK-92-CD3) were superinfected with four different TcRs, namely Radium-1 (TGFbRII frameshift specific, MHC-I)(FIG. 2B) and a cysteine variant, Radium-1$_{cys}$ (FIG. 2A), DMF-5 (MART-1 specific, MHC-I)(FIG. 2C), Radium-3 (hTERT specific, MHC-II)(FIG. 2D) and as a control cells not superinfected were run (FIG. 2E). Cells were stained with anti-CD3 to detect CD3 at the cell surface, and fluorescence was measured in the FITC (GFP) and APC (anti-CD3) channels. Cells in the top right quadrant express CD3 at the cell surface.

FIGS. 3A-3C show that Radium-1 (FIG. 3B) and DMF-5 TcRs (FIG. 3C) can be specifically detected at the surface of NK-92 cells expressing CD3-GFP. Cells were transfected to express CD3 and two different TcRs: Radium-1 (TGFbRII frame shift), DMF-5 (MART-1), and CD3 alone (NoTcR) (FIG. 3A). Cells were stained with a V-beta specific antibody that can detect Radium-1's V-beta chain (not DMFS, upper row) or a MART-1 multimer to detect the DMF-5 TcR at the cell surface (lower row). Fluorescence was measured in the FITC (GFP) and APC (anti-Vb and M1-multimer) channels.

FIG. 5 shows that a pure population of NK-92 cells CD3 superinfected with DMF-5 or Radium-1 TcRs and sorted are specifically activated by T2 cells loaded with the relevant peptide. Top: gating strategy: CD3 signal and GFP are used to separate the two cell lines. Then CD3+ population is tested for CD107a expression (degranulation). Histograms: the indicated NK-92-CD3-TcR were incubated with T2 cells loaded O/N with 1 µM of peptides (grey shading: no peptide, dark grey outline: MART-1, light grey outline: TGFbRII).

DETAILED DESCRIPTION

Figure 1:
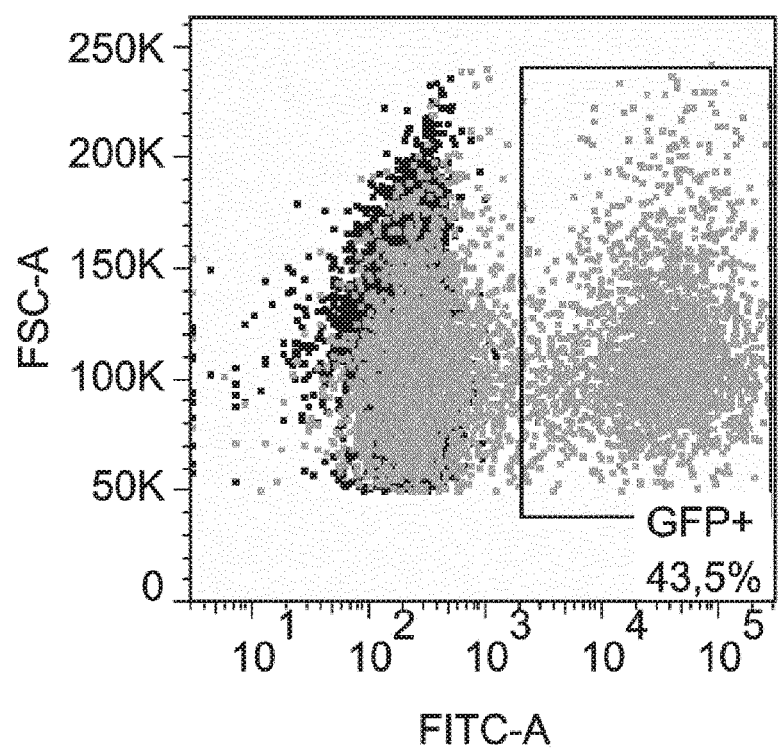
FIG. 1 shows that CD3 can be expressed in NK-92 cells. A CD3-IRES-GFP retroviral construct was transduced into NK-92 cells. Fluorescence was monitored in the FITC channel. GFP$^+$ cells are indicated in the marked region. Black: non transfected cells, grey: transfected cells.

Thus, in a first aspect, the present invention provides a modified NK cell, wherein said cell is non-immunogenic and is modified to express CD3.

In particular, the cell is modified to be non-immunogenic, for example by irradiation to reduce proliferative capacity, or by some other means of reducing proliferation, such that the cell does not persist for long enough to raise an immune response when introduced into a subject, or by modifying the cell to be MHC-negative.

The cells of the invention may further be modified to express a TcR having specificity towards an antigen on a target cell (i.e. a target antigen). As further defined below, the term "TcR" is used broadly herein to include any antigen receptor that comprises or is based on TcR antigen recognition regions, or is derived from a TcR. Thus, both native and synthetic TcRs e.g. TcR variants or derivatives are included.

In a particular embodiment, the present invention provides a non-immunogenic NK cell expressing CD3 and a TcR, wherein said TcR is specific for an antigen on a cancer cell. Put another way, the present invention provides a cancer-specific NK cell, wherein the cell is non-immunogenic and wherein the cancer specificity is provided by co-expression of a cancer-specific TcR and CD3. As will be described in more detail below, in a preferred embodiment the TcR is co-receptor independent, particularly CD4 and/or CD8 independent.

In a further aspect the present invention provides such cells as hereinbefore defined for use in therapy, more particularly for use in cancer therapy, or more generally in adoptive cell transfer therapy (e.g. in the treatment of any condition which may respond to T-cell therapy).

A still further aspect provides use of a modified NK cell as hereinbefore defined in the manufacture of a medicament for use in cancer therapy or for adoptive cell transfer therapy.

Also provided is a therapeutic composition comprising a modified NK cell as hereinbefore defined, together with at least one pharmaceutically acceptable carrier or excipient, and such a therapeutic composition for use in cancer therapy or in adoptive cell transfer therapy.

A yet further aspect provides a method of treatment, more particularly a method of cancer treatment, or a method of adoptive cell transfer therapy, which method comprises administering to a subject in need thereof (for example a subjected suffering from or diagnosed with cancer) an effective amount of a modified NK cell as hereinbefore defined.

For use in therapy, the modified NK cells of the invention will be modified to co-express a TcR with the CD3. Thus the preparation of a medicament or of a composition for use in therapy will comprise modifying the NK cell to express a TcR. The TcR will be designed or selected firstly to match the immune (i.e. MHC) type of the subject to be treated (i.e. the recipient of the modified NK cells) and secondly to match, or recognise, the cells in the subject to be targeted by the NK cells. That is the TcR is designed or selected to recognise a desired target antigen in the subject. This may be a target antigen expressed (or presented) by a cancer cell in the subject or by any cell which is to be abrogated by the adoptive cell transfer therapy e.g. an infected cell, for example a cell expressing (or presenting) a viral or other pathogen antigen.

Thus to perform cancer therapy or adoptive cell transfer therapy according to the invention, or to prepare a modified NK cell for therapeutic use, the following steps may be performed:

(a) providing a non-immunogenic NK cell which has been modified to express CD3;
(b) determining the MHC type of a subject to be treated;
(c) identifying a target antigen in the subject, which antigen is expressed or presented by cells in the subject, for example by identifying or determining the cancer type of the subject, and/or the expression of a particular cancer marker (e.g. antigen) or presence of a particular mutation etc.;
(d) modifying the cell of step (a) to express a TcR having specificity for the target antigen and matching the MHC type of the subject.

As will be discussed further below, the steps may be performed separately or sequentially, or simultaneously. Thus, for example, steps (a) and (d) may be performed simultaneously, more particularly the cell may be modified to express CD3 and a TcR in one or more simultaneous steps. However, in another embodiment the cell may be modified to express CD3 in a separate step prior to modification to express a TcR.

Finally, in a method of treatment or a therapeutic use, the modified cell of step (d) may be administered to the subject (e.g. in a further step (e)).

In another aspect of the present invention, a method is provided for the production of a universal NK cell (which cell is suitable for (or capable of) therapeutic use), or more particularly a universal NK cell for use in preparing a cell for personalised therapeutic use, namely for adoptive cell transfer therapy, said method comprising:

a) providing an NK cell which is non-immunogenic, more specifically modifying a NK cell to render it non-immunogenic; and b) modifying said cell to express CD3.

To further provide a modified NK cell for use in adoptive cell transfer therapy, the cell is further modified in step (c) to express a TcR, and in particular, for personalised therapy, a TcR which is matched to the MHC-type of the subject to be treated and which recognises a target antigen expressed or presented by a target cell to be targeted by the modified NK cell.

In a preferred embodiment, a method is provided for the production of a cancer-specific NK cell, said method comprising:

a) providing an NK cell which is non-immunogenic, e.g. modifying an NK cell to render it non-immunogenic;

b) modifying said cell to express CD3;

c) modifying said cell to express a cancer-specific TcR.

Steps (b) and (c) may be performed together (simultaneously) or separately, e.g. sequentially. However, in advantageous embodiments, as will be described further below, a universal NK cell may be prepared expressing CD3, which cell may subsequently be used in separate steps to prepare personalised cells for adoptive transfer therapy, by further modifying the cells to express a TcR which is selected based on the diagnosis and MHC-type of the subject. Thus a bank, or library, of TcR receptors may be prepared containing different TcRs (more specifically nucleic acid molecules or vectors encoding TcRs) according to MHC-specificity (i.e. type) and target antigen specificity (e.g. for a range of different known or previously identified target antigens e.g. cancer antigens). Depending on the diagnosis of the subject (e.g. a particular cancer type, or cancer known to express a particular antigen, or identified by specific analysis of the cancer of the subject), a particular TcR may be selected and used to modify the NK cell according to the invention. Alternatively, a bank or panel of modified NK cells may be prepared expressing both CD3 and TcRs of varying specificities, from which an appropriate NK cell may be selected depending on subject diagnosis and MHC-type.

Accordingly, a still further aspect of the present invention provides a combined product, or a kit, particularly such a product or kit for use in adoptive cell transfer therapy, or in cancer therapy, said product or kit comprising:

(a) a modified universal NK cell which is non-immunogenic and expresses CD3, more particularly an NK cell which is modified to be non-immunogenic and to express CD3; and (b) a panel of nucleic acid molecules each encoding a TcR, wherein the TcRs have different antigen specificity and/or different MHC specificity.

Conveniently the encoding nucleic acid molecules may be provided in vectors, for example vectors ready for introduction (i.e. transfection or transduction etc.) into the modified NK cell. In a preferred embodiment the TcRs have specificity for a cancer antigen, or for an antigen expressed, (e.g. preferentially or specifically) on cancer cells.

A yet further aspect of the invention provides a panel, or a library, of modified NK cells, each NK cell being non-immunogenic and expressing CD3, e.g. modified to be non-immunogenic and to express CD3, and expressing (i.e. being modified to express) a TcR, wherein the TcRs of different NK cells have different antigen specificity and/or different MHC specificity.

It will be understood that in such aspects there may be multiple TcRs recognising the same antigen but they may differ in their MHC specificity and vice versa.

The present invention employs cytotoxic cells of the immune system in the treatment of cancer. Specifically the present invention relates to the expression of TcRs in cytotoxic cells of the immune system which would otherwise not express a TcR, and methods that allow the expression of active, functional TcRs in such cells.

The terms 'cytolytic' and 'cytotoxic' are used interchangeably herein to refer to a cell capable of inducing cell death by lysis or apoptosis in a target cell.

The term 'target cell' refers to any cell which is killed by the cytotoxic cells of the invention. More particularly, the target cell is the cell targeted by the NK cells, and therefore a cell which expresses or presents an antigen recognised by the TcR (a target antigen). These may include any cell type, and are targeted by a cell of the invention via an antigen displayed on the surface of the target cell.

Thus the target cell may be any cell in the body of the subject which it is desired to abrogate, e.g. to remove, kill, render inactive etc. A preferred target cell is a cancer cell, but it may be any cell resulting from a disease or clinical condition. The disease or condition may thus be any condition that may benefit from adoptive cell transfer therapy, or more particularly from T-cell therapy targeting cells for killing or removal etc. As well as cancer cells, other cells that it may be clinically desirable to remove include infected cells, that is cells infected with any pathogen. Typically such cells will be virus-infected cells, but they may also be infected with any other pathogenic organism, e.g. any microorganism, for example, bacteria, fungi, mycoplasma, protozoa, prions. Alternatively, the target cell may be apoptotic or pre-apoptotic, or be in a stressed state (i.e. express stress-related markers at their cell surface), or may be a mutant cell, e.g. expressing a particular mutation.

The "target antigen" is (or more specifically provides or comprises) the molecule that is recognised by the TcR when presented on the target cell. Thus the target antigen, or more particularly a peptide derived from the target antigen, is presented on the target cell in an MHC-I or MHC II restricted manner, such as is required to be recognised by a TcR. Accordingly, as discussed above, the target antigen may be a cancer antigen, that is an antigen that is expressed specifically, selectively or preferentially by a cancer cell, or which is characteristic of a cancer cell or known or used as a cancer cell marker. The cancer antigen may be a universal cancer antigen, i.e. an antigen commonly found on a broad range of different cancers, or may be specific to a particular type of cancer. Alternatively, it may be an antigen from an infecting pathogen which is presented by the target cell, or any other antigen expressed or presented by any other cell it is desired to abrogate.

An 'MHC' refers to a protein of the major histocompatibility complex, and includes both MHCI and MHCII proteins. MHCII proteins are generally only found on the surface of antigen-presenting cells, such as dendritic cells, mononuclear phagocytes, some endothelial cells, and thymic epithelial cells. MHCII proteins are also expressed by B cells, and hence may be expressed by B-cell malignancies.

MHCII proteins are also frequently expressed by melanoma cells. The term MHC encompasses the human leukocyte antigen (HLA), and thus where the subject is human, these terms may be used interchangeably.

Any NK cell may be used according to the present invention. The term "NK cell" refers to a large granular lymphocyte, being a cytotoxic lymphocyte derived from the common lymphoid progenitor which does not naturally comprise an antigen-specific receptor (e.g. a T-cell receptor or a B-cell receptor). NK cells may be differentiated by their $CD3^-$, $CD56^+$ phenotype. The term as used herein thus includes any known NK cell or any NK-like cell or any cell having the characteristics of an NK cell.

In one embodiment, NK cells may be derived from a subject and grown in vitro to provide a population of NK cells for use in the present invention. NK cells may be autologous (i.e. derived from the subject to be treated using the cells and methods of the present invention), or may be heterologous (i.e. cells may be derived from a donor subject and may be intended for treatment of a second subject (i.e. they may be allogeneic, syngeneic or xenogeneic). Thus primary NK cells may be used. In an alternative embodiment, a NK cell known in the art that has previously been isolated and cultured may be used in the present invention. Thus a NK cell-line may be used. A number of different NK cells are known and reported in the literature and any of these could be used, or a cell-line may be prepared from a primary NK cell, for example by viral transformation (Vogel B et al. 2014 Leukemia 28:192-195). Cell lines may have a number of advantages over primary NK cells, for example they may be easier to grow and maintain in culture, more easily expanded and readily available on demand in standardised quality for adoptive cell transfer therapy. Certain cell lines, e.g. the NK-92 cell line, may also display higher cytotoxic activity, and in their unmodified state (that is not modified according to the present invention) they may have a broader spectrum of cell targets, e.g. cancer cell targets (this may be due to an absence or reduction in the number of inhibitory receptors). Suitable NK cells include (but are by no means limited to), in addition to NK-92, the NK-YS, NK-YT, MOTN-1, NKL, KHYG-1, HANK-1, or NKG cell lines.

In a preferred embodiment, the cell is an NK-92 cell (Gong et al., 1994, Leukemia 8, 652-658), or a variant thereof. A number of different variants of the original NK-92 cells have been prepared and are described or available, including NK-92 variants which are non-immunogenic. Any such variants can be used and are included in the term "NK-92". Variants of other cell lines may also be used. However, any NK-92 or indeed any NK cell for use according to the present invention should not be modified to express any antigen-specific receptor other than the TcR which is, or which is to be, introduced into the NK cell modified according to the present invention. For example, the cell should not express a CAR (a monoclonal antibody linked to an intracellular signalling domain from the TcR complex). More generally, the modified NK cell according to the invention does not express an antigen-specific receptor based on, or comprising, antibody recognition regions. An NK cell naturally does not comprise antigen-specific receptors, and thus the only antigen-specific receptor present in the cells of the invention is to be the TcR which is, or which is to be, introduced into the NK cell.

According to the present invention, the modified NK cell is non-immunogenic. Functionally speaking, this means that the cell is not recognised by the immune system of any subject into which it is introduced—it passes under the immunological radar and is not rejected or recognised as foreign by a recipient subject. That is to say, no clinically significant immunological response is raised against the modified NK cells by the immune system of the subject to whom the NK cells are administered. Thus a cell may be non-immunogenic if it does not, when administered to a subject, generate an immune response which affects, interferes with, or prevents the use of the cells in therapy.

The term "non-immunogenic" is thus used broadly herein to mean that when the cell is injected into or otherwise administered to a subject, there is no substantial or clinically significant immune response to the cell. More particularly, the cell does not raise (or is not capable of raising) an immune response sufficient to lead to rejection of the cell and/or to affect the function of the cells, e.g. the immune response is not sufficient to abrogate or to substantially or significantly reduce the function or effect (i.e. the utility) of the cells. Thus, the cells retain cytotoxic activity in the subject, more particularly significant or substantial or measurable cytotoxic activity against a target cell. In a particular embodiment, the cell is not rejected as foreign. As with any biological system, the absence of an immune response may not be absolute (or 100%), A small (or mild or minor) immune response to the NK cell (e.g. a de minimis immune response) may be tolerated, as long as the function or utility of the cells is not substantially affected (i.e. as long as the cells can still perform their function).

It will be seen, therefore, that an autologous cell (that is a cell administered to, or for administration, to the same subject from whom it was obtained) will be non-immunogenic (because it is "self"). Similarly, a non-autologous MHC-matched NK cell will be non-immunogenic, or substantially non-immunogenic. The term "non-immunogenic" thus includes functional non-immunogenicity. However, in certain embodiments, and as noted above, a non-immunogenic NK cell of the invention is non-immunogenic irrespective of the recipient of the cell, i.e. irrespective of the subject into whom it is, or is to be, introduced (i.e. it would not induce a clinically significant immune response if administered into a non-autologous subject). In particular embodiments, the NK cell may be subjected to a treatment which renders it non-immunogenic (i.e. it may be modified to be non-immunogenic). For example the treatment may be a physical, or chemical or biological treatment, or a structural or physico-chemical modification of the cells (e.g. a treatment which causes a structural or physical change or alteration of the cells), for example irradiation, or a genetic modification, e.g. to reduce or eliminate MHC expression by the cell. Accordingly, in some embodiments, the NK cell is not simply functionally immunogenic, but has or comprises a modification which renders it non-immunogenic.

Accordingly, NK cells may be naturally non-immunogenic, or may be modified to be non-immunogenic. Naturally non-immunogenic NK cells will not express the MHC molecule or only weakly express the MHC molecule, or may express a non-functional MHC molecule which does not stimulate an immunological response. NK cells which would be immunogenic may be modified to eliminate expression of the MHC molecule, or to only weakly express the MHC molecule at their surface. Alternatively, such cells may be modified to express a non-functional MHC molecule.

Any such cells (whether naturally non-immunogenic or modified in some way) do not comprise MHC at their surface at a sufficient level to trigger a clinically significant immunological response by a subject's immune response, and may be considered to be MHC-negative. In other words, an MHC-negative cell does not express on its surface any MHC molecule that is immunologically functional, or does not express on its surface MHC molecule at a sufficiently high level that it that may be recognised by another immune cell, particularly a non-self immune cell or an immune cell from an intended recipient subject. The cell may lack an MHC molecule, or it may not express MHC at its cell surface, or only weakly express MHC at its cell surface, or any MHC molecule that is expressed may be non-functional, e.g. it may be mutated or otherwise modified such that it is non-functional. Any means by which the expression of a functional MHC molecule is disrupted is encompassed. Hence, this may include knocking out or knocking down a molecule of the MHC complex, and/or it may include a modification which prevents appropriate transport to and/or correct expression of an MHC molecule, or of the whole complex, at the cell surface.

In particular, the expression of one or more functional MHC class-I proteins at the surface of a cell of the invention may be disrupted. In one embodiment the cells may be human cells which are HLA-negative and accordingly cells in which the expression of one or more HLA molecules is disrupted (e.g. knocked out), e.g. molecules of the HLA MHC class I complex.

In a preferred embodiment, disruption of MHC class-I may be performed by knocking out the gene encoding $\beta_2$-microglobulin, a component of the mature MHC class-I complex. Expression of $\beta_2$m may be eliminated through targeted disruption of the $\beta_2$-microglobulin gene ($\mu_2$m), for instance by site-directed mutagenesis of the $\beta_2$m promoter (to inactivate the promoter), or within the gene encoding the $\beta_2$m protein to introduce an inactivating mutation that prevents expression of the $\beta_2$m protein, e.g. a frame-shift mutation or premature 'STOP' codon within the gene. Alternatively, site-directed mutagenesis may be used to generate non-functional $\beta_2$m protein that is not capable of forming an active MHC protein at the cell surface. In this manner the $\beta_2$m protein or MHC may be retained intracellularly, or may be present but non-functional at the cell surface.

NK cells may alternatively be irradiated prior to being administered to a subject. NK-92 cells which have been irradiated have been found to be non-immunogenic in clinical trials and have been licenced for use in immunotherapy (Ton T. et al. 2013 Cytotherapy 15 1563-70). Without wishing to be bound by theory, it is thought that the irradiation of cells results in the cells only being transiently present in a subject, thus reducing the time available for a subject's immune system to mount an immunological response against the modified NK cells. Whilst such cells may express a functional MHC molecule at their cell surface, they may also be considered to be non-immunogenic.

Thus, a NK cell according to the invention may be modified to be non-immunogenic by reducing its ability, or capacity, to proliferate, that is by reducing its proliferative capacity.

A NK cell of the invention is modified to express CD3. As mentioned above, a NK cell of the invention does not express a CAR, or indeed any antigen-specific receptor other than a TcR. Thus, in particular, except in the case of a TcR-CD3 fusion, the CD3 is not expressed as part of a chimeric receptor. More particularly, the CD3 is not expressed as part of a chimeric antigen receptor (CAR), or any chimeric receptor based on (or comprising) antibody-derived antigen binding region(s), or a binding domain derived from any binding molecule or moiety which is not a TcR, e.g. from any other affinity binding partner, for example from a ligand or receptor other than a TcR. Thus, the CD3 is not expressed as part of a chimeric receptor which comprises an antigen binding domain (i.e. a binding part, or moiety) or any binding domain or ligand which is not a TcR or which is not derived from a TcR. In other words, the CD3 is expressed independently (i.e. as a separate molecule or chain, or not as part of a fusion with a moiety which is not a CD3 chain or a part thereof, or a spacer or linker molecule), and/or it is expressed as part of (or within) a TcR-CD3 fusion. Accordingly, in particular, a NK cell of the invention does not express a CAR or other chimeric receptor which comprises a CD3 chain or molecule, other than a CD3-TcR fusion. In an embodiment where the CD3 is provided as, or as a part of fusion (i.e. a fusion protein), it is a CD3 fusion or a CD3-TcR fusion, as described further below.

NK cells do not normally (or natively) express CD3 and hence to render the cell capable of expressing CD3 a nucleic acid molecule encoding CD3 is introduced into the cell. Thus the cell is modified to recombinantly express CD3. In other words the cell is modified to permit expression of a heterologous nucleic acid molecule encoding CD3. The CD3 may be matched to the species of the cell (i.e. of the same species as the cell), however, CD3 from a different species may also be used. Thus, for a human NK cell human CD3, or CD3 from another mammalian species, such as mouse, rat, rabbit etc. may be expressed. In a preferred embodiment all of the chains of CD3 (i.e. a CD3γ chain, a CD3δ chain, two CD3ε chains and the ζ chain) are expressed in an NK cell. However, it is also contemplated that only a single CD3 chain (e.g. only the CD3γ chain, or only the CD3δ chain, or only the CD3ζ chain, or only the CD3ε chain, or any combination thereof, is present. Thus an NK cell may be modified to express any of the CD3 chains singly, or in combination with other CD3 chains, up to and including the complete CD3 molecule. Without wishing to be bound by theory, it is hypothesised that it may be possible to direct a TcR to the cell surface and/or initiate signalling where one or more of the CD3 chains is not expressed in an NK cell. It is also anticipated that one or more of the chains of CD3 may be provided as a fusion protein, wherein at least two of the chains are expressed as a single polypeptide, provided that the localisation and signalling functions of CD3 are retained.

The one or more CD3 chains may also be encoded by one nucleic acid molecule or more than one nucleic acid molecule, e.g. on separate molecules. Conveniently a construct will be made which comprises a nucleic acid molecule encoding all three CD3 chains, e.g. under the control of the same promoter or linked to each other in some way.

A NK cell of the invention may further be modified to express a TcR. A TcR may be viewed as any receptor comprising a TcR antigen-recognition domain, antigen-recognition sequence, or fragment thereof which selectively binds to an antigen on the surface of a target cell. Thus in the context of the present invention a TcR may be a canonical TcR comprising a TcR antigen-recognition domain in its native (or natural) context, or it may comprise a TcR antigen-recognition domain, antigen-recognition sequence, or fragment thereof linked to an amino acid sequence and/or protein domains (i.e. as part of a chimeric molecule or fusion protein) which are not naturally found together in a TcR (i.e. a non-native context). The term "TcR" is thus used broadly herein to include any antigen receptor wherein the antigen recognition region is provided by a TcR antigen-recognition domain or sequence, e.g. an antigen recognition region from a native TcR, or derived from a native TcR. The term "TcR"

accordingly includes native and non-native TcRs, that is synthetic or artificial TcR molecules or constructs, TcR variants or derivatives, or a TcR molecule derived from or based on a native TcR.

An NK cell expressing a TcR thus has antigen-specific (i.e. targeted) cytotoxic activity towards a target cell. The TcR may be any TcR having specificity towards an antigen on a target cell of interest (a target antigen). The specificity of the NK cell, (i.e. the antigen to which the cell binds) will be determined by the specificity of the TcR. In other words, selection of a suitable TcR is necessary to provide an NK cell having the desired specificity (i.e. specificity towards a specific antigen on a target cell). Thus in one embodiment the present invention provides an NK cell modified to express CD3 and further modified to express a TcR having specificity towards an antigen on a target cell.

In a preferred embodiment, the TcR binds to an antigen on the surface of a target cell with high affinity (i.e. the TcR is a high affinity TcR). In such an advantageous embodiment, the TcR is capable of binding to MHC-antigen complex on the surface of the target cell with sufficiently high affinity that the cell expressing the TcR is capable of undergoing activation in the absence of the CD8/CD4 coreceptors typically required for the activation of a TcR in a cytotoxic or helper T cell, respectively. Thus the present invention provides an NK cell modified to express CD3 and further modified to express a TcR having specificity towards an antigen on a target cell, wherein said TcR binds to said target cell with high affinity and undergoes activation in the absence of the CD8 and/or CD4 coreceptors. Alternatively expressed, the TcR which is introduced into the NK cell according to the present invention is co-receptor (or cofactor) independent; that is it does not require a further receptor or cofactor for the cell to be activated (i.e. for signalling in the cell induced by TcR binding to occur). Thus the TcR may bind to the antigen (the MHC-antigen complex) with a $k_{off}$ within the normal physiological range. In particular it is CD8- and/or CD4-independent, e.g. CD8-independent, and more particularly CD4 and CD8-independent. However, in an alternative embodiment the NK cell may be further modified to express CD4 and/or CD8.

A TcR recognises and binds to an antigen (a peptide) presented at the cell surface by a protein of the MHC class-I or -II family. The recognition of the antigen thus depends on both the MHC-type of the cell and the peptide (more specifically the sequence of the peptide) (antigen). Generally speaking the target antigen is known and the TcR is selected according to its antigen specificity. In a preferred embodiment, the sequence of peptide antigen presented by a target cell may be known. Additionally, the MHC-type of a target cell may also be known. Thus in a preferred embodiment, a TcR may be selected that is capable of specifically binding to an antigen-MHC complex on the surface of a target cell. Thus in a preferred embodiment the present invention provides an NK cell modified to express CD3 and further modified to express a TcR having specificity towards an antigen on a target cell, wherein said TcR is capable of specifically binding to an antigen-MHC complex on the surface of a target cell.

In a preferred embodiment of the invention, a TcR may be selected from a cytotoxic T-cell that has been identified as specifically displaying cytotoxicity towards a target cell or a helper T-cell. Alternatively, the antigen-recognition domain or sequence of such a TcR, or a fragment thereof may be selected. Said T-cell may be obtained from a patient that will be the subject of treatment, or may be obtained from a second subject (i.e. a TcR donor). Thus, a TcR may be selected from a T-cell identified as having "proven" activity against a target cell. In other words, a TcR can be selected which has been shown to be effective against the target cell. By way of example, T-cells, e.g. tumour-infiltrating lymphocytes, may be isolated from a cancer patient. By their nature these will be, or will include, T-cells which are active against the cancer of the patient. The genes encoding the TcR of such cells can be identified and cloned, and used to express the TcR, or the antigen-recognition domain or sequence of such a TcR, or a fragment thereof, in an NK cell according to the invention. The T-cells may be produced in the patient or in a subject by vaccination e.g. by administration of vaccine comprising a cancer antigen. Those T-cells induced by the vaccination which are most active against a cancer in the subject, or against cancer cells, may then be selected. In such a way the most potent or effective TcRs may be selected, e.g. TcRs with the highest affinity or which are co-receptor independent. Affinity maturation may be undertaken to obtain an optimal TcR.

Advantageously, the HLA profile or MHC profile of the subject from which the TcR is derived (TcR donor) will be the same as the HLA profile or MHC of the subject to be treated. As noted above, a TcR in a T-cell having specificity towards a target cell may be identified and characterised, and the amino acid sequence of the TcR and the nucleic acid sequence of the gene encoding the TcR may be obtained. Put another way, a cytotoxic T-cell or a helper T-cell comprising a TcR having specificity for a particular antigen on a target cell may be identified in a subject, and the amino acid sequence of the receptor and the DNA sequence of the gene encoding the receptor may be obtained. The DNA sequence or the gene may be used to prepare a nucleic acid molecule or construct for introduction into an NK cell to allow that TcR to be expressed in the host (i.e. recipient) NK cell.

In an alternative embodiment of the invention, an artificial TcR (i.e. a TcR not identified from a cytotoxic or helper T-cell) may be used. The TcR may be an artificially-generated allo-reactive TcR. The binding domain of a TcR may be generated by a combinatorial-based method, such as phage display or ribosome display, and a chimeric protein comprising an artificial binding domain, specific for a particular antigen and MHC (e.g. HLA) combination, may be obtained.

The TcR may be provided as a construct, or fusion, comprising other protein domains.

One or more of the CD3 chains (or the entire CD3 construct) may be expressed as a fusion protein with the TcR. In other words, one or more of the CD3 chains may be present in the same polypeptide chain as the TcR. In a preferred embodiment, the CD3 molecule, or one or more of the CD3 chains (e.g. the CD3γ chain, the CD3δ chain, the CD3ζ chain, or the CD3ε chain, or any combination thereof) may be present as a TcR-CD3 fusion construct that will be directly targeted to the plasma membrane, i.e. without a requirement for a further CD3 molecule to also be present in the cell (as long as the fusion construct retains a transmembrane domain, e.g. provided by a CD3 chain (Willemsen R M 2000 Gene Therapy 7:1369-1377). Thus in such an embodiment the cell may be modified to express CD3 and a TcR simultaneously, as part of the same construct or fusion. Although a separately expressed CD3 may not be necessary, it may nonetheless be provided, for example to improve signalling and hence cell activity.

As noted above, a panel of different TcRs may be developed, each TcR in the panel having specificity for (e.g. specific affinity towards) a particular antigen-MHC complex. Thus, different target antigens may be recognised, and/or different epitopes on a target antigen, and/or the TcRs may have differing affinity and/or selectivity for an antigen. Additionally, for a given target antigen, the panel may comprise TcRs of different MHC specificity (or MHC type). In this way, a particular TcR that is capable of binding to a specific antigen-HLA complex may be selected from the panel for use in the methods of the invention, that is a TcR which matches both the target antigen and the MHC-type of a subject. Thus, in a particularly preferred embodiment, a specific TcR may be selected based on the nature of the antigens presented by a particular target cell, and its MHC (e.g. HLA) type. It is anticipated that such a panel may be used to allow the rapid generation of an NK cell having specific cytotoxic activity towards a target cell. Accordingly, a method of the present invention for producing an NK cell having specificity for a target cell may comprise:

a) modifying an NK cell to express CD3;

b) determining the MHC profile of said target cell and the identity of an antigen displayed by said target cell; and c) modifying said NK cell to express a TcR, wherein said TcR is selected from a panel of TcRs each having specificity for a different antigen and/or MHC-type, and wherein said TcR has specificity for the MHC and antigen displayed on said target cell.

The TcRs may be provided in the panel in the form of nucleic acid molecules comprising nucleotide sequences encoding the TcRs. Conveniently, the nucleic acid molecules may be comprised within vectors or constructs, particularly vectors or constructs suitable directly for introduction into a NK cell. The nucleic acid molecule may be DNA or RNA. For example the TcRs may be provided as mRNA or as viral vectors, e.g. retroviral vectors.

In one embodiment, an NK cell is modified to express a TcR after the cell is modified to express CD3. Thus, as noted above, a universal NK cell may be prepared by modifying a non-immunogenic NK cell to express CD3. Such modified NK cells may be grown and maintained in culture, or stored for future use. Accordingly, in one embodiment the cell may be allowed to replicate to produce a population of NK cells expressing CD3, prior to modifying the cells to express a TcR. The NK cells may be grown in culture, or expanded. In an alternative embodiment it is contemplated that the cell may be modified to express CD3 and a TcR at the same time, or substantially at the same time. In one embodiment, a single vector or construct comprising genes for both CD3 and a TcR may be used to modify a cell to express both CD3 and TcR, and in other embodiments separate vectors may also be used. As discussed above, fusion protein comprising both TcR and CD3 functionalities in a single polypeptide molecule may also be expressed in NK cells, and thus a vector or construct encoding such a fusion protein may be used to modify a cell. NK cells modified to express both CD3 and a TcR may be allowed to replicate, e.g. may be grown in culture or expanded prior to introducing the cells into a subject. Thus in an embodiment of the present invention, a population of NK cells expressing CD3 may be generated, and a sub-population of NK:CD3 cells may be modified to express a TcR having specificity to an antigen on the surface of a target cell.

The modified NK cells of the invention may also be subject to modification in other ways, for example to alter or modify other aspects of cell function or behaviour, and/or to express other proteins. For instance, the cells may be modified to express a homing receptor, or localisation receptor, which acts to target or improve the localisation of the cells to a particular tissue or location in the body. Cells may also be modified to express one or more of the components of the T-cell signalling pathway, in order to enhance the cytotoxic response exhibited by the NK cells. Any such modification may take place before, after or simultaneously with modification according to the present invention.

The cell of the invention may be modified to alter its ability to replicate in vivo and/or in vitro. In one embodiment, the replicative capacity of the cell (the ability of a cell to replicate i.e. to proliferate) may be enhanced. In a preferred embodiment, this may be achieved by modifying the cells to have enhanced expression of a cytokine, such as IL-2. IL-2 is generally required for NK cells to grow and maintain cytolytic function, and thus cells expressing IL-2 do not require additional IL-2 to be supplemented in growth medium, and retain cytotoxic activity when introduced into a subject. Expression of a cytokine may be enhanced by introducing a heterologous (non-native) vector or construct comprising a nucleic acid molecule encoding a cytokine into a cell, or alternatively, expression of an endogenous gene encoding a cytokine may be enhanced. Expression of a cytokine may be constitutive (i.e. the promoter controlling expression of the gene encoding a cytokine may be constitutively active, or 'on'), or may be inducible by an external stimulus.

In one embodiment the cell may be modified to have enhanced replicative capacity before the cell is modified to express CD3 and/or a TcR. In another embodiment, the cell may be modified to have enhanced replicative capacity after the cell is modified to express CD3 and/or a TcR. In an alternative embodiment, the cell may be modified to have enhanced replicative capacity after the cell is modified to express CD3, but before the cell is modified to express a TcR (i.e. it may thus be possible to produce a large population of NK cells expressing CD3, prior to modifying the cells to express a TcR). Alternatively, any two or more of the above modifications may be performed at substantially the same time. In one embodiment, all three modifications may be performed at substantially the same time.

Proliferative capacity and viability (survival) of NK cells of the present invention may also be reduced before the cell is introduced into a patient. As noted above, this may be done to render the cell non-immunogenic. In a preferred embodiment, the replicative capacity and/or viability of the cell may be reduced by irradiation. The ability of a cell to replicate and/or its viability may be diminished (i.e. replication may take place more slowly) or eliminated depending on the dose and nature of irradiation supplied to the cells. Radiation may be from any source of $\alpha$, $\beta$ or $\gamma$ radiation, or may be X-ray radiation or ultraviolet light. A radiation dose of 5-10 Gy may be sufficient to abrogate proliferation, however other suitable radiation doses may be 1-10, 2-10, 3-10, 4-10, 6-10, 7-10, 8-10 or 9-10 Gy, or higher doses such as 11, 12, 13, 14, 15 or 20 Gy. Alternatively, the NK cells may be modified to express a 'suicide gene', which allows the cells to be inducibly killed or prevented from replicating in response to an external stimulus.

A cell may be modified A) to have enhanced replicative capacity and B) to have reduced replicative capacity and/or viability. The two modifications may be performed sequentially in any order (i.e. A then B, or B then A), or may be performed at essentially the same time (A and B together). In such an embodiment, the cell may be modified to express a cytokine (such as IL-2) to enhance growth of the cells in vitro before, at the same time, or after modifying the cell to express CD3 and/or a TcR and may subsequently be modified to have its replicative capacity and/or viability reduced prior to introducing the cell into a subject.

It will be clear from the foregoing that a cell of the invention may be modified to alter the level of expression of one or more genes, or in particular to allow the expression of one or more genes which are not normally expressed by the cell. To allow such heterologous gene expression, a nucleic acid molecule corresponding to, or comprising, the gene in question is introduced into the cell. Conveniently the nucleic acid molecule may be introduced into the cell in a vector or recombinant construct. Methods of heterologous gene expression are known in the art, both in terms of construct/vector preparation and in terms of introducing the nucleic acid molecule (vector or construct) into the cell. Thus, promoters and/or other expression control sequences suitable for use with mammalian cells, in particular lymphoid cells or NK cells, and appropriate vectors etc (e.g. viral vectors) are well known in the art.

Vectors or constructs (nucleic acid molecules) may be introduced into a cell of the invention by a variety of means, including chemical transfection agents (such as calcium phosphate, branched organic compounds, liposomes or cationic polymers), electroporation, cell squeezing, sonoporation, optical transfection, hydrodynamic delivery, or viral transduction. In a preferred embodiment, a vector or construct is introduced by viral transduction. Heterologous nucleic acid molecules introduced into a cell may be expressed episomally, or may be integrated into the genome of the cell at a suitable locus.

Cell culture methods and reagents suitable for NK cells are also well known in the art. Any desired method of cell culture may be used, according to choice and convenience etc. For example, Teflon bags may be used for large scale culture, or automated cell culture systems.

The target cell of the invention may be a cancer cell. Cancer is defined broadly herein to include any neoplastic condition, whether malignant, pre-malignant or non-malignant. Generally, however, it may be a malignant condition. Both solid and non-solid tumours are included and the term "cancer cell" may be taken as synonymous with "tumour cell".

Any type of cancer is encompassed, including both solid and haematopoietic cancers. Representative cancers include Acute Lymphoblastic Leukaemia (ALL), Acute Myeloid Leukaemia (AML), Adrenocortical Carcinoma, AIDS-Related Cancer (e.g. Kaposi Sarcoma and Lymphoma), Anal Cancer, Appendix Cancer, Astrocytomas, Atypical Teratoid/Rhabdoid Tumour, Basal Cell Carcinoma, Bile Duct Cancer, Extrahepatic Bladder Cancer, Bone Cancer (e.g. Ewing Sarcoma, Osteosarcoma and Malignant Fibrous Histiocytoma), Brain Stem Glioma, Brain Cancer, Breast Cancer, Bronchial Tumours, Burkitt Lymphoma, Carcinoid Tumour, Cardiac (Heart) Tumours, Cancer of the Central Nervous System (including Atypical Teratoid/Rhabdoid Tumour, Embryonal Tumours, Germ Cell Tumour, Lymphoma), Cervical Cancer, Chordoma, Chronic Lymphocytic Leukemia (CLL), Chronic Myelogenous Leukaemia (CML), Chronic Myeloproliferative Disorder, Colon Cancer, Colorectal Cancer, Craniopharyngioma, Cutaneous T-Cell Lymphoma, Bile Duct Cancer, Extrahepatic Ductal Carcinoma In Situ (DCIS), Embryonal Tumours, Endometrial Cancer, Ependymoma, Esophageal Cancer, Esthesioneuroblastoma, Ewing Sarcoma, Extracranial Germ Cell Tumour, Extragonadal Germ Cell Tumour, Extrahepatic Bile Duct Cancer, Eye Cancer (including Intraocular Melanoma and Retinoblastoma), Fibrous Histiocytoma of Bone, Gallbladder Cancer, Gastric (Stomach) Cancer, Gastrointestinal Carcinoid Tumour, Gastrointestinal Stromal Tumours (GIST), Germ Cell Tumor, Gestational Trophoblastic Disease, Glioma, Hairy Cell Leukaemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumours, Pancreatic Neuroendocrine Tumours, Kaposi Sarcoma, Kidney Cancer (including Renal Cell and Wilms Tumour), Langerhans Cell Histiocytosis, Laryngeal Cancer, Leukaemia (including Acute Lymphoblastic (ALL), Acute Myeloid (AML), Chronic Lymphocytic (CLL), Chronic Myelogenous (CML), Lip and Oral Cavity Cancer, Liver Cancer (Primary), Lobular Carcinoma In Situ (LCIS), Lung Cancer, Lymphoma, Macroglobulinemia, Waldenström, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Childhood, Multiple Myeloma/Plasma Cell Neoplasm, Mycosis Fungoides, Myelodysplastic Syndromes, Myelodysplastic/Myeloproliferative Neoplasms, Multiple Myeloma, Myeloproliferative Disorders, Nasal Cavity and Paranasal Sinus Cancer, Nasopharyngeal Cancer, Neuroblastoma, Non-Hodgkin Lymphoma, Non- Small Cell Lung Cancer, Oral Cancer, Oral Cavity Cancer, Oropharyngeal Cancer, Osteosarcoma, Ovarian Cancer, Pancreatic Cancer, Pancreatic Neuroendocrine Tumours (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Urethral Cancer, Uterine Cancer, Endometrial, Uterine Sarcoma, Vaginal Cancer, Vulvar Cancer, Waldenström Macroglobulinemia, and Wilms Tumour As noted above, a number of cancers have been identified to express particular or specific cancer antigens, or to be characterised by expression of particular or specific cancer antigen. Thus a known or recognised cancer antigen may be used. As is known in the art, certain antigens may occur in a number of different cancer types, others may be specific for a particular cancer type. However, in other cases it may be appropriate or necessary to characterise the cancer in a subject and to identify a cancer antigen suitable for use. Thus any cancer may be treated using a TcR directed against a universal cancer antigen and such TcRs have been identified. Alternatively, the cancer may be any cancer which is presently treated, or proposed for treatment, by adoptive T-cell therapy, e.g. common cancers such as melanoma, haematological cancers, lung cancer, colorectal cancer. Further alternatively, the cancer may be a rare cancer where few treatment options are presently available (e.g. with orphan drug status), such as e.g. pancreatic cancer or sarcoma.

In other embodiments the target cell may be an infected cell, and in particular a cell infected with a virus. The virus may be any virus, but generally will be a pathogenic virus. By way of example, the virus may be HIV, a hepatitis virus (e.g. HBV or HCV), HPV, CMV or EBV, HHV-8, HTLV-1, SV40, enterovirus. Other possible infective agents or pathogens include also bacteria, e.g. Helicobacter pylori, Chlamydia pneumoniae, and parasites e.g. Schistosoma haematobium and the liver flukes, Opisthorchis viverrini, Clonorchis sinensis and malaria.

In one embodiment of the present invention the cells may be administered to a subject directly intravenously. In an alternative embodiment the cells may administered directly into a tumour via intratumoural injection.

The dose of cells administered to a subject will vary depending on the nature of the target cell. In a preferred embodiment of the invention where the target cell is a cancer cell, the dose may be calculated based on the type of cancer which is to be targeted. In a preferred embodiment, a dose of approximately $10^9$ cells may be administered to the subject, however this may be varied depending on the type and extent of the cancer. It is possible that a dose of approximately $10^6$, $10^7$, or $10^8$ cells may be administered. Alternatively, a higher dose of approximately $10^{10}$, $10^{11}$ or $10^{12}$ cells may be administered. The dose of cells administered may also be varied depending on the patient's body size, and thus a dose of $10^5$, $10^6$, $10^7$, $10^8$, $10^9$, $10^{10}$, $10^{11}$ or $10^{12}$ cells may be administered per m² of the patient's body surface area or per kg of the patient's weight.

It is also anticipated that multiple infusions may be required in order to treat a subject effectively. For example, 2, 3, 4, 5, 6 or more separate infusions may be administered to a patient, at intervals of 24 or 48 hours, or every 3, 4, 5, 6 or 7 days. Infusions may also be spaced at weekly, fortnightly or monthly intervals, or intervals of 6 weeks or 2, 3, 4, 5, or 6 months. It is also possible that yearly infusions may be administered.

The subject to be treated using the methods and cells of the present invention may be any species of mammal. For instance, the subject may be any species of domestic pet, such as a mouse, rat, gerbil, rabbit, guinea pig, hamster, cat or dog, or livestock, such as a goat, sheep, pig, cow or horse. In a further preferred embodiment of the invention the subject may be a primate, such as a monkey, gibbon, gorilla, orang-utang, chimpanzee or bonobo. However, in a preferred embodiment of the invention the subject is a human.

It is contemplated that NK cells for use in the present invention may be obtained from any species of mammal, however, in a preferred embodiment the NK cells will be from the same species of mammal as the subject to be treated. Furthermore, and as noted above, in a preferred embodiment the cell will be modified using genes expressing proteins from the same species of mammal (e.g. human CD3 and TcR will be used for a human subject). It is possible however that a CD3 and TcR from different species may also be used, for instance a cell may be modified using genes expressing a mouse CD3 and a human TcR.

EXAMPLE 1

Expression of CD3 in NK92 Cells

A codon-optimised pMP71-CD3ζ-CD3ε-CD3γ-CD3δ-IRES-GFP (CD3-GFP) vector (Ahmadi et al. 2011. Blood 118, 3528-3573) was used to transfect NK92 cells with CD3, and cells were transfected using retroviral transduction. Retrovirus containing the CD3-GFP construct was produced in packaging cell line (Hek-Phoenix) and NK cells were spinoculated (0.3 M cells with incubated with viral supernatant and spun down at 900×g for 1 hour at 32 C on retronectin (Tanaka Biotech) coated plates). GFP was used as a marker for successful transduction.

Successful transduction of NK-92 cells with CD3 (NK-92(CD3)) was confirmed by flow cytometry using a FACS Canto flow cytometer (BD Biosciences). Fluorescence was monitored in the SSC and FITC channels, and successful transfection was observed by monitoring fluorescence in the GFP channel (see FIG. 1). A transfection efficiency of approximately 50% was obtained. Alternatively GFP+ cells were sorted in order to obtain a pure population.

EXAMPLE 2

Expression of TcR in NK-92(CD3) Cells

The ability of NK-92(CD3) cells to co-express CD3 and a TcR was tested. CD3 and TcRs each require the co-expression of the other member of the TcR complex in order to be targeted to the cell surface. It was thus possible to use the expression of CD3 on the surface of the NK cells as a marker for the successful co-transfection of a cell with both CD3 and a TcR.

NK-92(CD3) cells were super infected with four different TcRs using retroviral supernatants (a Radium-1$_{cys}$ cysteine variant, Radium-1-specific (TGFbRII frameshift), DMF-5, MART-1 specific (DMF-5 (Johnson, L. A. et al. 2006 J Immunol 177:6548-6559)) and Radium-3 (hTERT, MHC-II)) and expression of CD3 at the cell surface was monitored for each TcR using an anti-CD3 antibody multimer labelled with APC. Expression of CD3 was detected by monitoring the cells for GFP expression. Fluorescence was detected in the FITC and APC channels. Cells expressing GFP appear in the right hand region of the dot plots, and cells expressing CD3 at their cell surface appear in the upper region of the dot plots. Cells co-expressing CD3 and TcR (i.e. cells with the CD3-TcR complex localised at the cells surface) appear in the upper right region of the dot plots.

Expression of CD3 at the cell surface was detected cells modified to express each of the TcRs (FIGS. 2A-2D) (cells in the upper-right quadrant in each dot plot). In particular, cells modified to express the Radium-1 TcR showed expression of CD3 at the cell surface FIG. 2B. FIG. 2D also shows a small increase in fluorescence in the APC channel for GFP⁺ cells, indicating a low level of expression of the Radium-3 TcR. No CD3 expression is detected at the cell surface for cells lacking a TcR (FIG. 2E).

Expression of the TcRs at the cell surface was also detected in NK-92(CD3) cells modified to express the Radium1 and DMF-5 TcRs. The presence of the TcR at the cell surface was monitored using either a V-beta specific antibody that can detect Radium-1's V-beta chain or a MART-1 multimer to detect the DMF-5 TcR at the cell surface (lower row), labelled with APC. Fluorescence was measured in the FITC (GFP) and APC (anti-Vb and M1-multimer) channels. No increase in signal was seen in the APC channel for NK-92(CD3) cells not modified to express a TcR (FIG. 3A). Cells modified to express the Radium-1 TcR showed an increase in signal in the APC channel when stained with the ant-Vβ3 antibody but not the MART-1 multimer. (FIG. 3B). Cells modified to express the DMF-5 TcR showed an increase in signal in the APC channel when stained with the MART-1 multimer (FIG. 3C).

EXAMPLE 3

NK-92(CD3) Expressing a TcR are Functional

In order to validate the functionality of our TcR when expressed in an NK cell, we tested whether the TcR expressed in the NK cells was capable of specifically recognising target cells.

NK-92(CD3) cells expressing a TcR were incubated with target cells expressing a single chain trimer (SCT) molecule comprising the correct target peptide (TGFbRII), or a non-specific peptide (irr) for 5 hours, or in the absence of target cells (No APC), and expression of the degranulation marker CD107 was monitored as a marker for the ability of the NK cells to be stimulated by the target cells. (SCTs represent an MHC class-I protein displaying an antigen, and consist of an antigen peptide, $\beta_2$-microglobulin and h-chain expressed as a single polypeptide chain, see US 2010/015954 and Yu, Y. Y.et al.(2002) J Immunol 168: 3145-3149.

Figure 4A:
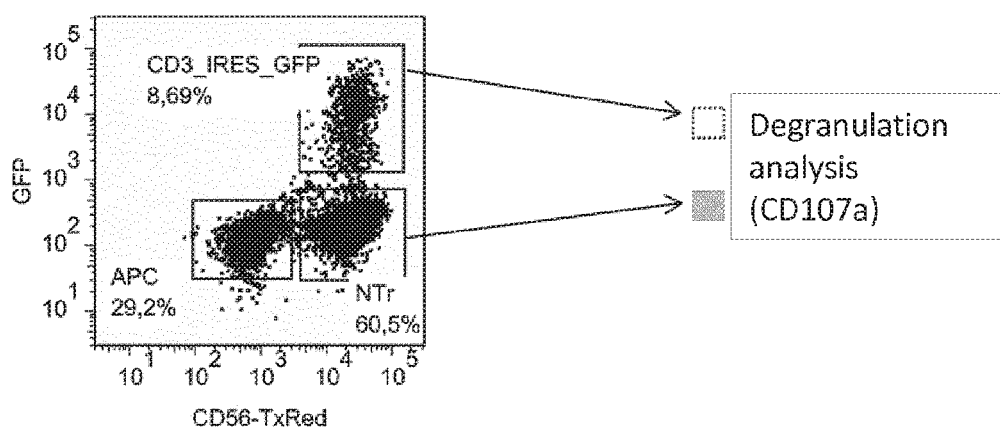
FIGS. 4A-4D show that NK-92 cells modified to express CD3 and Radium-1 TcR demonstrate antigen-specific cytotoxic activity. NK-92 cells transfected with CD3-IRES-GFP (GFP$^+$—upper box—CD3_IRES_GFP)(FIG. 4A) and cells which were not transfected (GFP$^-$—lower box—NTr) (FIGS. 4B-4D) were gated into two separate populations. NK cells were incubated with SupT1 cells expressing single chain trimer with the TGFbRII target peptide, and irrelevant peptide or alone. The SupT1 cells were separated from the NK cells by detecting the expression of the NK cell marker CD56. Degranulation was monitored by detection of the CD107 marker in NK cells after incubation with the SupT1 cells in the GFP$^+$ and GFP$^-$ populations, and plotted together (histogram, grey: GFP$^-$, dashed: GFP$^+$).

NK-92(CD3) cells were initially stained with anti-CD56 Tx Red (CD56 is a marker for NK cells) and TxRed and GFP fluorescence was monitored (FIG. 4A). Separate populations of NK-92 cells were observed based on the expression of GFP. GFP$^+$ cells (upper region) and GFP$^-$ NK cells (lower region) were both detected. The expression of CD107a was monitored for each population of cells, and GFP$^-$ cells were used as a negative control (i.e. non-TcR expressing cells).

Figure 4B:
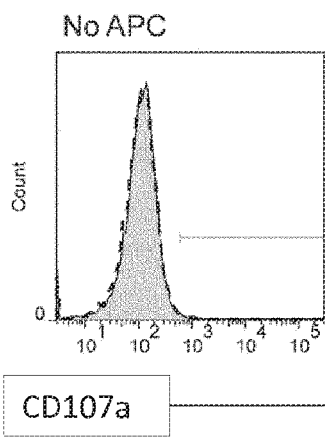
Figure 4C:
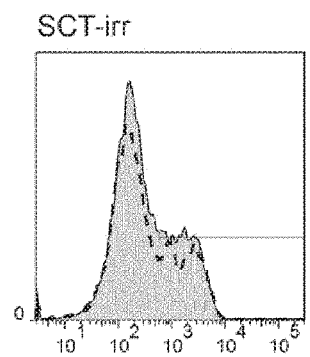
Figure 4D:
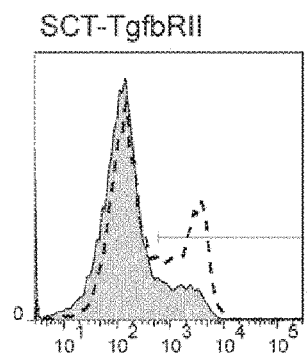

NK-92(CD3) cells expressing Radium1-specific TcR were incubated with SupT1 expressing a single chain trimer (SCT) molecule with the a non-specific peptide (FIG. 4C) or the Radium-1 target peptide TGFbRII (FIG. 4D). Cells incubated in the absence of an antigen-presenting cell were also monitored (FIG. 4B) CD3 expression was monitored for the NK-92 cell line and cells were gated as outlined above. GFP$^+$ (dotted line) and GFP$^-$ (solid line) populations are visible in each histogram.

Only NK-92(CD3) cells expressing the Radium-1-specific TcR showed an increase in CD107 expression when incubated with SupT1 cells expressing the Radium-1 SCT (FIG. 4D), as indicated by the rightwards shift of the dotted line compared with the solid line (GFP$^-$ negative control). No increase in CD107 expression was seen for these cells when incubated with SupT1 cells expressing the non-specific peptide (FIG. 4C) or cells incubated in the absence of the antigen presenting cells.

Together, these data indicate that NK-92(CD3) expressing the Radium-1-specific TcR are able to be activated by target cells expressing the Radium-1 target peptide. This demonstrates that the TcR expressed in NK-92(CD3) cells is active and functional. NK-92(CD3) cells expressing a TcR are thus shown to have target-cell specific cytotoxicity.

EXAMPLE 4

Activation of NK-92(CD3) Cells Expressing TcRs by T2 Cells Loaded with the Relevant Peptide NK-92(CD3) cells were modified to express either the Radium-1 or DMF-5 TcRs and expression of CD3 at the cell surface was detected using APC-labelled anti-CD3. CD3$^+$ cells were selected for degranulation analysis (FIG. 5, top panel) and sorted.

NK-92(CD3) cells modified to express the Radium-1 or DMF-5 TcRs were incubated with T2 cells (FIG. 5, bottom panels) loaded with either the TGFbRII (light grey outline) or MART1 (dark grey outline) peptides, which are the target antigens for the Radium-1 and DMF-5 TcRs respectively. CD107a expression by NK-92(CD3) cells expressing the Radium-1 (FIG. 5, bottom left pane) and DMF-5 (FIG. 5, bottom right panel) TcRs incubated with T2 cells in the presence of either peptide was measured. NK-92(CD3) cells modified to express the Radium-1 TcR exhibited activation in the presence of the TGFbRII peptide, and cells expressing the DMF-5 TcR exhibited activation in the presence of MART-1. No non-specific activation was seen.

Figure 6:
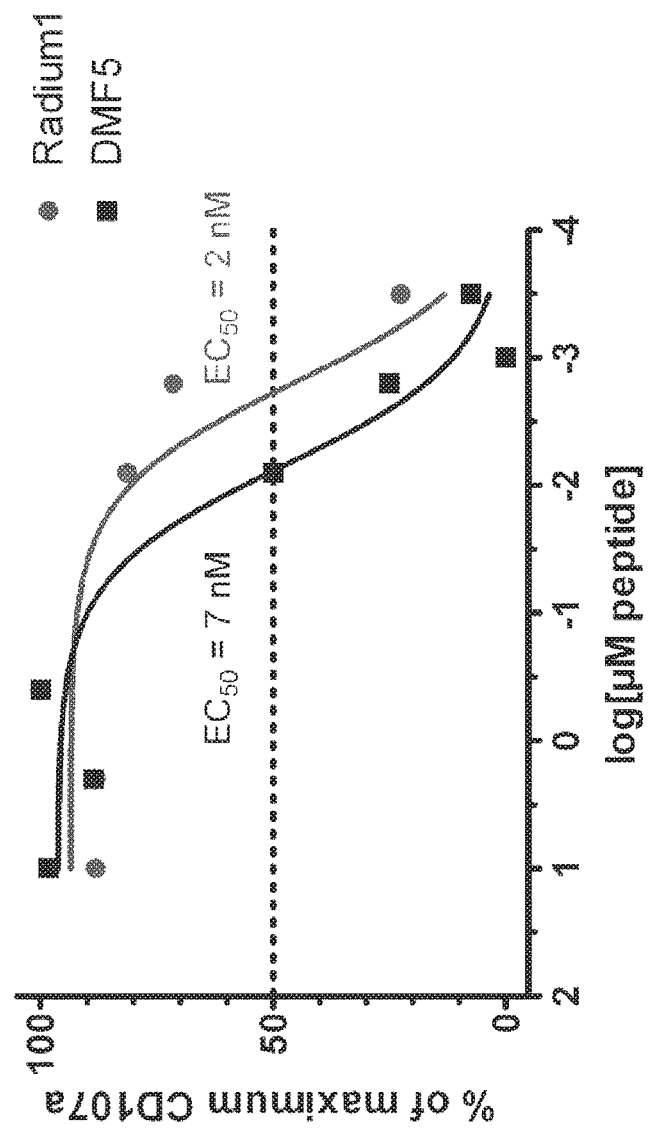
FIG. 6 shows the calculation of EC50 values for the Radium-1 and DMF-5 TcRs.

A similar experiment was also performed to determine the EC$_{50}$ for each TcR. NK-92(CD3) cells modified to express the Radium-1 (circles) and DMF-5 (squares) TcRs were incubated with T2 cells in the presence of the TGFbRII or MART-1 peptides respectively at a range of different peptide concentrations. Activation was measured by detecting CD107a expression as outlined above. Expression of CD107a was measured at each concentration, and relative activation (CD107a as a percentage of maximum CD107a expression) was calculated. EC$_{50}$ values of 2 nM (Radium-1) and 7 nM (DMF-5) were calculated (FIG. 6).

EXAMPLE 5

Figure 7:
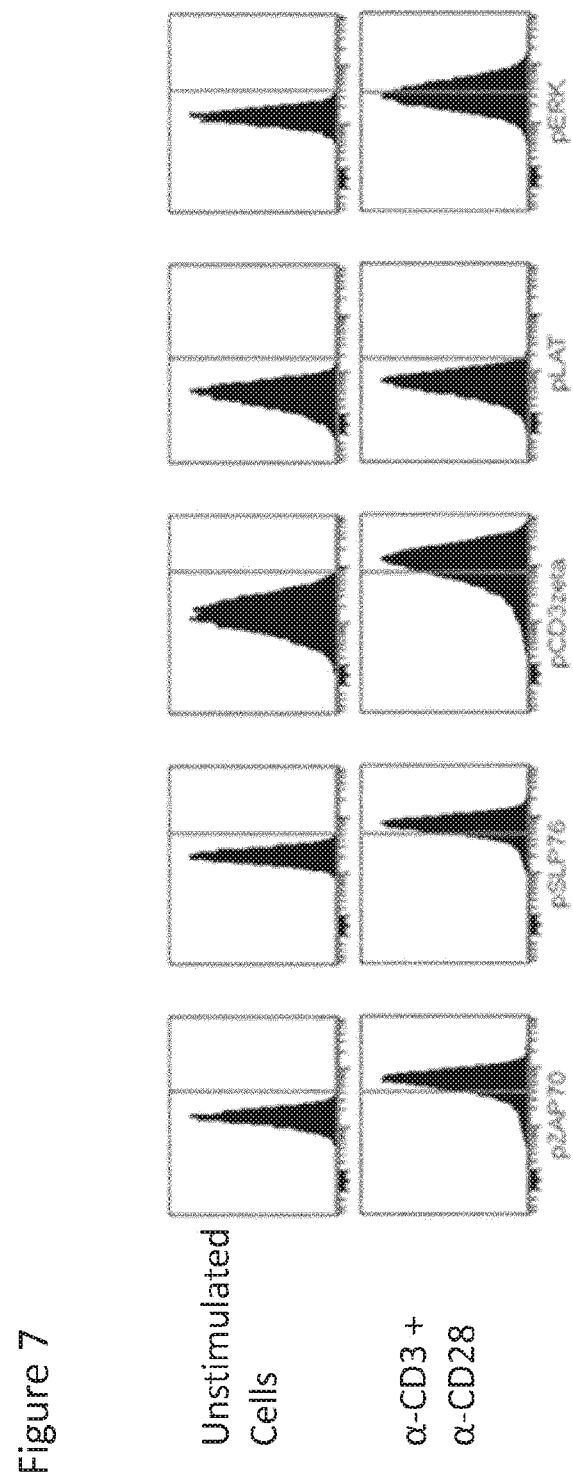
FIG. 7 shows the results of Phospho-flow cytometry analysis of the activation of NK-92(CD3/Radium-1) cells upon contacting with α-CD3 and α-CD28 antibodies. Right-shifts of the flow cytometry spectra indicate increased levels of phosphorylation of the relevant protein, which in turn indicates activation of the TCR complex.

TcR/CD3-Mediated Signalling in NK-92(CD3) Cells
NK-92(CD3) cells transfected with the Radium-1 TcR were tested using Phospho-flow cytometry to investigate their signalling ability. Initially, the general signalling ability of the TCR complex was analysed by stimulating cells with anti-CD3 and anti-CD28 antibodies, which simulates activation through the TCR. As shown in FIG. 7, the clustering of TcR and CD3 leads to the activation of a signalling cascade similar to the one observed in T cells. This is shown by the increased levels of phosphorylation of several TcR/CD3-related proteins, including ZAP-70, SLP-76 and CD3.

Figure 8:
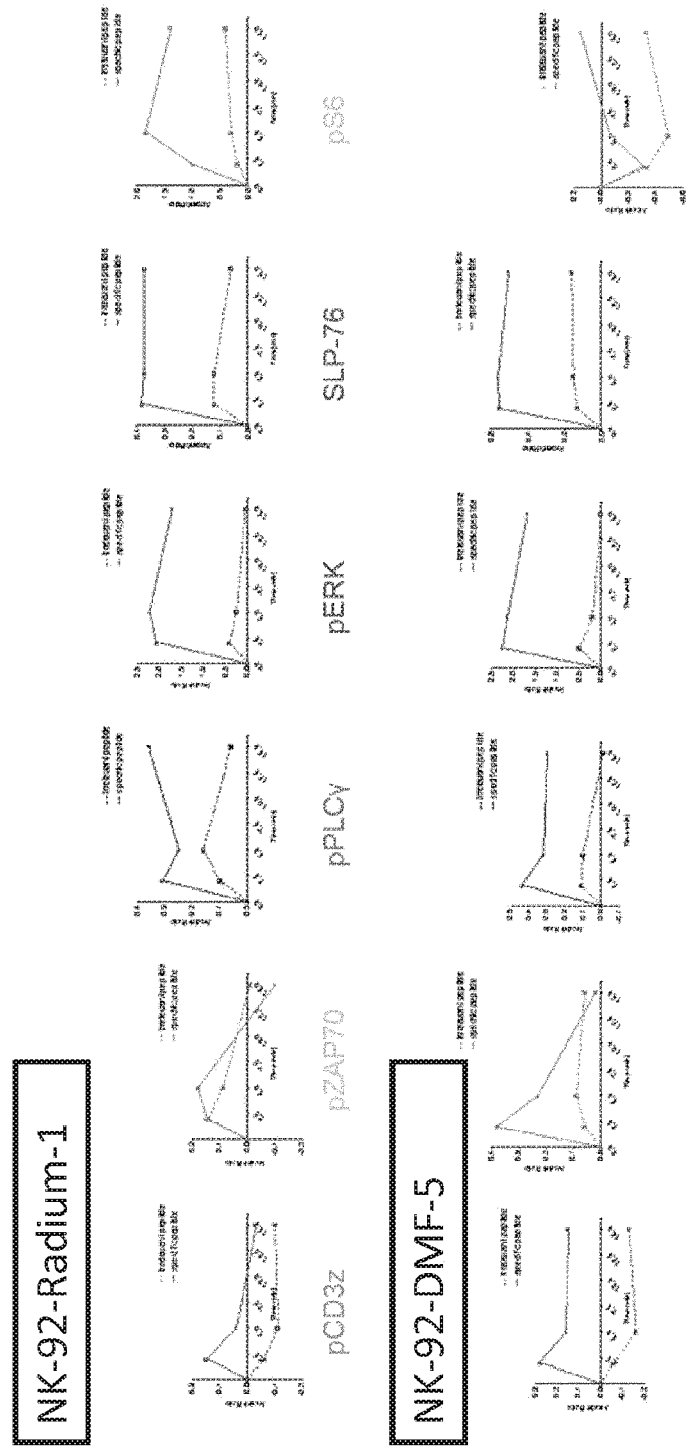
FIG. 8 shows the specificity of stimulation of NK-92 (CD3/Radium-1) and NK-92(CD3/DMF-5) cells. NK-92 cells were incubated with antigen-presenting cells, presenting either the specific, cognate peptide for each receptor (TGFbRII for cells expressing Radium-1, MART-1 for cells expressing DMF-5) or a random peptide. Stimulation of signalling through the TCR complex was measured at various time-points according to the level of phosphorylation of various TcR/CD3-related proteins. These levels of phosphorylation were measured by Phospho-flow cytometry. In each graph, the continuous line defines activation of the cells by the specific, cognate peptide; the dotted line defines activation of the cells by the random peptide.

The cells were then tested for stimulation by specific antigens, using antigen-presenting cells and monitoring the signalling activity of the TCR complexes at different time points by Phospho-flow cytometry. Both NK-92(CD3)-Radium-1 and NK-92(CD3)-DMF-5 were stimulated with their cognate peptides. As shown in FIG. 8, only specific stimulation led to signalling molecule phosphorylation. Early and late signals could be distinguished, and the pattern was similar to that seen in T cells. Taken together, these data demonstrate that NK-92(CD3-TCR) react like T cells when in contact with their substrate.

EXAMPLE 6

Stimulation of NK-92(CD3) Cells by CD4$^+$ T Cell-Derived TcRs

Figure 9:
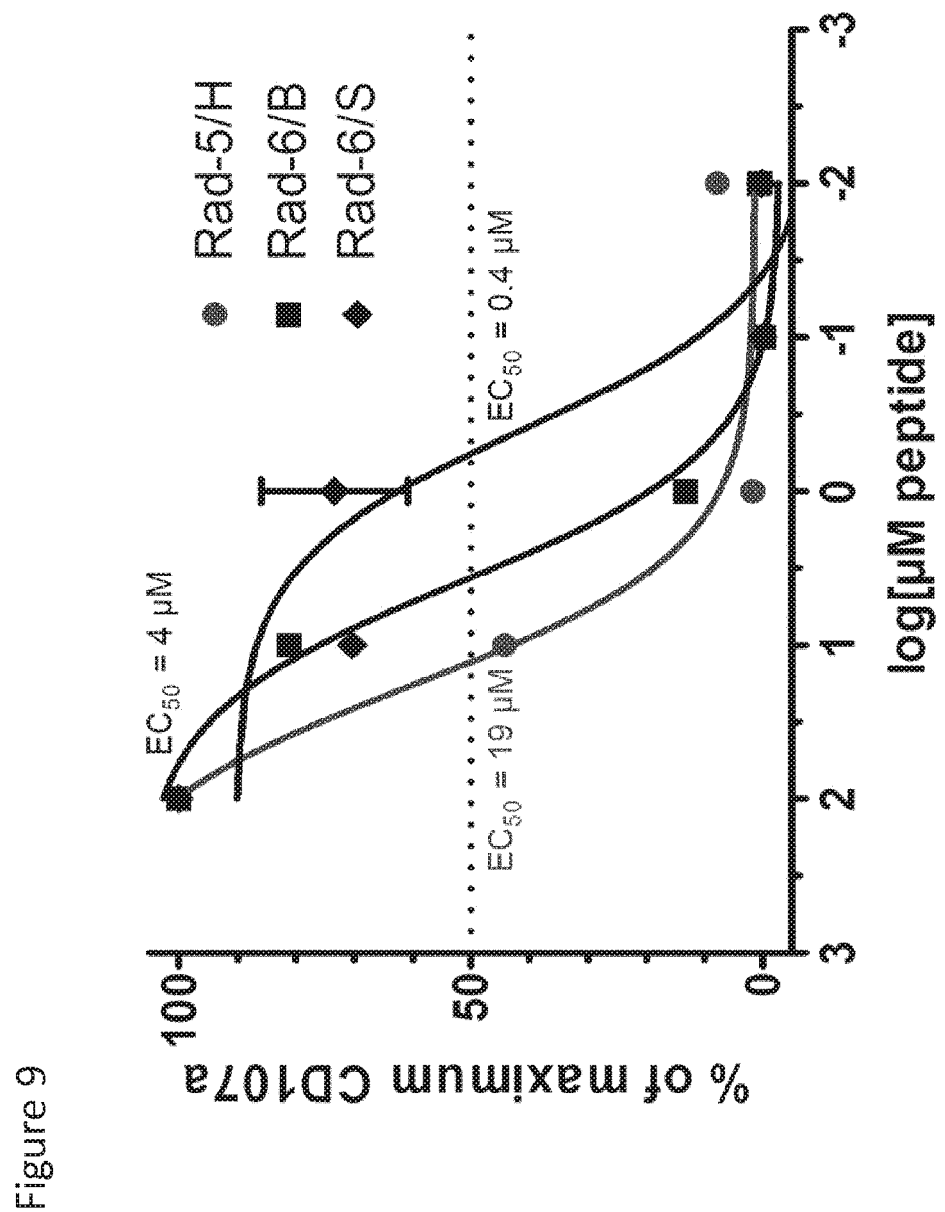
FIG. 9 shows the kinetics of stimulation of NK-92(CD3) cells transduced with either the Radium-5 or Radium-6 TcR. Both of these receptors are derived from CD4$^+$ T cells and specifically bind a TGFbRII frameshift peptide; Radium-5 specifically binds it in the context of HLA-DR7, Radium-6 in the context of HLA-DR4. The EC$_{50}$ values for Radium-5 and Radium-6 are calculated using tissue from donor patients (patients H, S and B). Patient H has the HLA-DR7 haplotype; patients S and B have the HLA-DR4 haplotype.

The CD4$^+$ T cell-derived TcRs Radium 5 and Radium 6 were transduced into NK-92(CD3) cells. These TcRs were able to redirect the cells specifically against MHC Class II peptide targets. Both Radium-5 and Radium-6 specifically target a TGFbRII frameshift mutant peptide (KSLVRLSS-CVPVALMSAMT, SEC) ID NO: 1); Radium-5 targets this peptide specifically in the context of HLA-DR7, Radium-6 in the context of HLA-DR4. The kinetics of the stimulation of NK-92(CD3)-Radium-5/6 cells is shown in FIG. 9. NK-92(CD3) cell stimulation is measured as in Example 4, above. EC$_{50}$ values for both TcRs were calculated, as shown in FIG. 9. The Radium-5 EC$_{50}$ in an HLA-DR7 haplotype patient sample was calculated as 19 μM; the Radium-6 EC$_{50}$ was calculated as 4 μM in one patient sample and 0.4 μM in a second. Both patient samples were of the HLA-DR4 haplotype.

EXAMPLE 7

Analysis of NK-92 Protein Expression with and without CD3/CD3-TcR Expression

Protein expression profiles of NK-92 cells were compared with those of NK-92(CD3/CD3-TcR) cells. No change was seen between the two groups of cells (save of course the presence of CD3 on NK-92(CD3/CD3-TcR) cells. The comparison is shown in the table below (PBMC=Peripheral Blood Mononuclear Cells).

| Surface Markers | NK-92 | NK-92 652 (CD3-transduced) | PBMCs |
|---|---|---|---|
| CD3 | − | (+) | + |
| CD4 | − | − | + |
| CD8 | − | − | + |
| CD16 | − | − | + |
| CD25 | + | + | + |
| CD28 | + | + | + |
| CD45RA | + | + | + |
| CD45RO | + | + | + |
| CD56 | + | + | + |
| CD57 | + | + | + |
| CD62L | − | − | − |
| CD134 (OX40) | + | + | + |
| CD152 (CTLA-4) | + | + | (+) |
| CD336 (NKp44) | − | − | − |
| CD337 (NKp30) | + | + | + |
| PD1 | + | + | + |
| HLA cl I | + | + | + |
| HLA-DR | − | − | − |
| CXCR3 | + | + | + |
| CXCR4 | + | + | + |
| NKG2D | + | + | + |

The invention claimed is:

1. A natural killer (NK) cell which does not naturally express a T cell receptor (TcR) and which is modified by recombinant expression to express a recombinant TcR exogenous to the cell, wherein:
 (i) said cell expresses CD3 chains CD3γ, CD3δ, CD3ε and CD3ζ, and the CD3 chains and the recombinant TcR form a functional CD3-TcR complex located at the surface of the NK cell; and
 (ii) said recombinant TcR is an antigen receptor which comprises a TcR antigen-recognition domain and does not comprise an antibody antigen-recognition domain.

2. The cell according to claim 1, wherein said cell is modified to be non-immunogenic.

3. The cell according to claim 1, wherein said NK cell is an NK-92 cell.

4. The cell according to claim 1, wherein the cell is;
 i) modified to disrupt or prevent expression of β$_2$ microglobulin; or
 ii) human and human leukocyte antigen (HLA)-negative, or
 iii) irradiated, or its proliferative capacity is otherwise reduced.

5. The cell according to claim 1, wherein the recombinant TcR is CD8- and/or CD4-independent.

6. The cell according to claim 1, wherein the recombinant TcR has specificity towards an antigen on a cancer cell or an infected cell.

7. The cell according to claim 1, wherein the recombinant TcR is specific for both an antigen expressed by a target cell in a subject to be treated by administration of the cell and for the MHC type of the subject.

8. A therapeutic composition comprising the modified NK cell as defined in claim 1, together with at least one pharmaceutically acceptable carrier or excipient.

9. The cell according to claim 1, wherein said recombinant TcR is not expressed as a fusion protein with a CD3 chain.

10. The cell according to claim 1, wherein no CD3 chain is expressed as part of a fusion protein with a moiety which is not a CD3 chain or a part thereof.

11. The cell according to claim 1, wherein said recombinant TcR is not expressed as part of a fusion protein.

12. The cell according to claim 1, wherein said NK cell is a primary NK cell.

13. A kit for use in adoptive cell transfer therapy, said kit comprising:
 (a) an NK cell which does not naturally express a T cell receptor (TcR) and expresses CD3 chains CD3γ, CD3δ, CD3ε and CD3ζ; and
 (b) a panel of vectors each comprising a nucleic acid molecule encoding a recombinant TcR, wherein each recombinant TcR is an antigen receptor comprising a TcR antigen-recognition domain and not comprising an antibody antigen-recognition domain, and wherein each of the recombinant TcRs have different antigen specificity and/or different MHC specificity.

14. The kit according to claim 13, wherein said NK cell is:
 i) modified to disrupt or prevent expression of β$_2$ microglobulin; or
 ii) human and HLA-negative; or
 iii) irradiated, or its proliferative capacity is otherwise reduced.

15. The kit according to claim 13, wherein said vectors are viral vectors.

16. The kit according to claim 13, wherein said NK cell is non-fetal.

* * * * *

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Synthetic peptide

<400> SEQUENCE: 1

Lys Ser Leu Val Arg Leu Ser Ser Cys Val Pro Val Ala Leu Met Ser
1               5                   10                  15

Ala Met Thr